(12) United States Patent
Yi et al.

(10) Patent No.: US 10,041,951 B2
(45) Date of Patent: Aug. 7, 2018

(54) IMAGING PROBE INCLUDING NANOPARTICLE

(71) Applicant: Massachusetts Institute of Technology, Cambridge, MA (US)

(72) Inventors: Hyunjung Yi, Cambridge, MA (US); Debadyuti Ghosh, Cambridge, MA (US); Jifa Qi, Cambridge, MA (US); Angela M. Belcher, Lexington, MA (US); Michael S. Strano, Lexington, MA (US); Neelkanth M. Bardhan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1099 days.

(21) Appl. No.: 13/755,613

(22) Filed: Jan. 31, 2013

(65) Prior Publication Data

US 2013/0230464 A1 Sep. 5, 2013

Related U.S. Application Data

(60) Provisional application No. 61/593,058, filed on Jan. 31, 2012.

(51) Int. Cl.
| | |
|---|---|
| *G01N 33/58* | (2006.01) |
| *A61K 49/00* | (2006.01) |
| *B82Y 10/00* | (2011.01) |
| *B82Y 15/00* | (2011.01) |

(52) U.S. Cl.
CPC ....... *G01N 33/582* (2013.01); *A61K 49/0017* (2013.01); *A61K 49/0056* (2013.01); *A61K 49/0058* (2013.01); *A61K 49/0095* (2013.01); *B82Y 15/00* (2013.01); *Y10S 977/75* (2013.01); *Y10S 977/927* (2013.01)

(58) Field of Classification Search
None
See application file for complete search history.

(56) References Cited

U.S. PATENT DOCUMENTS

| | | | |
|---|---|---|---|
| 2007/0292896 A1* | 12/2007 | Strano et al. | 435/7.9 |
| 2008/0063587 A1* | 3/2008 | Strano et al. | 423/447.1 |
| 2009/0304581 A1* | 12/2009 | Scheinberg et al. | 424/1.53 |
| 2010/0279421 A1* | 11/2010 | Strano et al. | 436/86 |
| 2011/0257033 A1* | 10/2011 | Strano et al. | 506/9 |
| 2012/0178640 A1* | 7/2012 | Strano et al. | 506/9 |

OTHER PUBLICATIONS

Welsher, et al. ("A route to brightly fluorescent carbon nanotubes for near-infrared imaging in mice" Nat Nanotechnol. Nov. 2009; 4(11): 773-780.).*
Liang, et al. ("A Review on Biomedical Applications of Single-Walled Carbon Nanotubes" Current Medicinal Chemistry, 2010, 17, 10-24).*
Smith, et al. ("Second window for in vivo imaging" Nat Nanotechnol vol. 4, No. 11, 2009, pp. 710-711).*
Kelly et al. ("In vivo imaging of molecularly targeted phage" Neoplasia . vol. 8, No. 12, Dec. 2006, pp. 1011-1018).*
Li, K. et al.("Chemical modification of M13 bacteriophage and its application in cancer cell imaging" Bioconjugate Chem. 21, 2010, 1369-1377).*
Hong, S. Y. et al. ("Filled and glycosylated carbon nanotubes for in vivo radioemitter localization and imaging" Nature Materials 2010, 9 (6), 485-490).*
Liu et al. ("Drug delivery with carbon nanotubes for in vivo cancer treatment" Cancer Res. Aug. 15, 2008; 68(16): 6652-6660.).*
Iverson et al. ("In Vivo Biosensing Via Tissue Localizable Near Infrared Fluorescent Single Walled Carbon Nanotubes" Nat Nanotechnol. Nov. 2013 ; 8(11): 873-880. doi:10.1038/nnano.2013.222).*
Flynn et al. ("Viruses as vehicles for growth, organization and assembly of Materials" Acta Materialia 51 (2003) 5867-5880).*
He et al. ("Near-infrared fluorescent nanoprobes for cancer molecular imaging: status and challenges" Trends Mol Med. Dec. 2010 ; 16(12): 574-583. doi:10.1016/j.molmed.2010.08.006).*
Hyunjung Yi ("M 13 virus/single-walled carbon nanotubes as a materials platform for energy devices and biomedical applications" Thesis, Sep. 2011, Massachusetts Institute of Teclmology).*
Chu et al., Attaching quantum dots to HER2 specific phage antibodies, Adv. Nat. Sci: Nanosci. Nanotechnol., 2, (2010), (4 pages).*
Walling et al., Quantum dots for live cell and in vivo Imaging, Int. J. Mol. Sci., 10, (2009), p. 441-491.*
International Search Report and Written Opinion dated Jun. 12, 2013 for PCT/US2013/024069.
Yi, Hyunjung "M13 virus/single-walled carbon nanotubes as a materials platform for applications," Thesis (Ph.D) Massachusetts Institute of Technology, Dept. of Materials Science and Engineering, 2011, Massachusetts Institute of Technology, US , Sep. 1, 2011, pp. 1-178.
Yi, Hyunjung et al. "M13 Phage-Functionalized Single-Walled Carbon Nanotubes as Nanoprobes for Second Near-Infrared Window Fluorescence Imaging of Targeted Tumors," Nano Letters, vol. 12, No. 3, Jan. 23, 2012, pp. 1176-1183.

* cited by examiner

*Primary Examiner* — Ram R Shukla
*Assistant Examiner* — Ellen J Marcsisin
(74) *Attorney, Agent, or Firm* — Foley & Lardner LLP

(57) ABSTRACT

An imaging probe can include a photoluminescent carbon nanostructure configured to emit a wavelength of light detectable through living tissue, and a targeting moiety including a first binding partner configured to interact with a second binding partner.

33 Claims, 21 Drawing Sheets

IMAGING PROBE INCLUDING NANOPARTICLE

CLAIM OF PRIORITY

This application claims priority to provisional U.S. Patent Application No. 61/593,058, filed Jan. 31, 2012, which is incorporated by reference in its entirety.

GOVERNMENT SPONSORSHIP

This invention was made with government support under Grant No. U54 CA151884 awarded by the National Institutes of Health. The government has certain rights in this invention.

TECHNICAL FIELD

This invention relates to an imaging probe including a nanoparticle which can be coupled with a novel imaging technology.

BACKGROUND

Fluorescence imaging is a powerful imaging modality for non-invasive and non-radiative detection of diseases and monitoring of treatment response. Nanomaterials show great promise as imaging agents due to their intrinsic properties, including photoluminescence.

SUMMARY

Stable, biocompatible, and sufficiently bright emissive nanomaterials, such as, for example, carbon nanotubes, including single walled carbon nanotubes (SWNTs), can be used to develop methods or material systems that provide targeted nanomaterials having bright enough emission for in vivo imaging.

In one aspect, an imaging probe can include a photoluminescent nanostructure. A photoluminescent nanostructure can be configured to emit a wavelength of light detectable through living tissue. A photoluminescent nanostructure can be configured to emit a wavelength of light in the near infrared spectrum. For example, a photoluminescent nanostructure can be configured to emit a wavelength of light at least 650 nm, at least 700 nm, at least 750 nm, at least 800 nm, at least 850 nm, at least 900 nm, at least 950 nm, at least 1000 nm, at least 1050 nm, at least 1100 nm, at least 1150 nm, at least 1200 nm, at least 1250 nm, at least 1300 nm, or at least 1350 nm. Additionally, a photoluminescent nanostructure can be configured to emit a wavelength of light of at most 700 nm, at most 750 nm, at most 800 nm, at most 850 nm, at most 900 nm, at most 950 nm, at most 1000 nm, at most 1050 nm, at most 1100 nm, at most 1150 nm, at most 1200 nm, at most 1250 nm, at most 1300 nm, or at most 1350 nm. Preferably, a photoluminescent nanostructure can be configured to emit a wavelength of light in the second near-infrared window of light (i.e. from 950-1400 nm).

In some embodiments, a living tissue can be at least 0.1 cm, at least 0.25 cm, at least 0.5 cm, at least 0.75 cm, at least 1 cm, at least 1.5 cm, at least 2 cm, at least 2.5 cm, at least 3 cm, at least 4 cm, at least 5 cm thick or more.

In some embodiments, an imaging probe can include a targeting moiety that can direct to a region or a targeting moiety can concentrate or bind an imaging probe in a region. In some cases, a targeting moiety can include a first binding partner configured to interact with a second binding partner.

In some embodiments, a second binding partner can include a tissue-type specific or cell-type specific molecule. Tissue-types can include connective tissue, muscle tissue (e.g. smooth muscle, skeletal muscle or cardiac muscle), nervous tissue (e.g. central nervous system tissue, peripheral nervous system tissue, motor neurons, ganglia), or epithelial tissue (e.g. skin or digestive tract). Other tissue types can include organ-type specific molecule (e.g. lung, liver, renal, blood, heart, brain, stomach, colon, etc.). Cell-types can include normal cell-types or abnormal cell-types. For example, a cell-type specific molecule can be a molecule associated with a disease state, such as cancer.

In some embodiments, a second binding partner can include a nucleic acid, a carbohydrate, a lipid, a peptide or a protein. In some embodiments, a first binding partner can include a nucleic acid, a carbohydrate, a lipid, a peptide or a protein. In some embodiments, a first binding partner can include at least a portion of an antibody. A portion of an antibody can be the $F_v$ region or the $F_{ab}$ region.

In some embodiments, a first binding partner can include at least a portion of a ligand and the second binding partner can include a receptor, or vice versa.

In some embodiments, a targeting moiety can include at least one viral protein. The at least one viral protein can be a M13 bacteriophage protein, for example, p1, p2, p3, p4, p5, p6, p7, p8, p9, p10 or p11. In some embodiments, an at least one viral protein can be a capsid protein.

In some embodiments, a first binding partner and an at least one viral protein can be bound together. In some embodiments, a first binding partner and an at least one viral protein can comprise a chimeric protein.

In some embodiments, a first binding partner can be configured to interact with a second binding partner in vivo. In other words, a first binding partner can be configured to interact with a second binding partner in a living mammal. In some embodiments, a first binding partner can be configured to interact with a second binding partner ex vivo, for example, in a tissue or cell culture.

In some embodiments, a photoluminescent nanostructure can be a carbon nanostructure. In some cases, a carbon nanostructure can be a carbon nanotube. More specifically, in some cases, a carbon nanotube can be a single walled carbon nanotube.

In some embodiments, the targeting moiety can include *Escherichia coli.*, which can express F-pili appendages. In some embodiments, the targeting moiety can include a biotin acceptor peptide. In some embodiments, the targeting moiety can include a secreted protein, acidic and rich in cysteines (SPARC) binding peptide.

In some embodiments, the imaging probe can include an anti-bacterial antibody, an M13, and a carbon nanotube. The anti-bacterial antibody can include an anti-*Staphylococcus aureus* antibody. In some embodiments, the imaging probe can include a secreted protein, acidic and rich in cysteines (SPARC) binding peptide, an M13, and a carbon nanotube.

In some embodiments, the imaging probe can have a binding affinity for tumors located at various lengths in a body, for example, at depths of 9.7 to 18.2 millimeters. In some embodiments, there can be a differential binding affinity between a tumor and healthy tissue.

In some embodiments, the imaging probe can have a fluorescence stability of at least 24 hours in vivo. In some embodiments, the probe can have a fluorescence stability across a 4 pH unit range from PH 4.5 to PH 8.5. In some embodiments, the imaging probe is not cytotoxic to an ovarian cell line.

In one aspect, a method can include applying an imaging probe to a sample. A sample can include a cell, a tissue, an organ or a mammal.

In some embodiments, a method can include exposing at least a portion of the sample to a stimulus. A stimulus can include a light, a pH, a temperature or the level of an analyte (e.g. oxygen). More specifically, a stimulus can be an excitation light.

In some embodiments, a method can include detecting an emission from the imaging probe. An emission can be a wavelength of at least 650 nm, at least 700 nm, at least 750 nm, at least 800 nm, at least 850 nm, at least 900 nm, at least 950 nm, at least 1000 nm, at least 1050 nm, at least 1100 nm, at least 1150 nm, at least 1200 nm, at least 1250 nm, at least 1300 nm, or at least 1350 nm. Additionally, an emission can be a wavelength of at most 700 nm, at most 750 nm, at most 800 nm, at most 850 nm, at most 900 nm, at most 950 nm, at most 1000 nm, at most 1050 nm, at most 1100 nm, at most 1150 nm, at most 1200 nm, at most 1250 nm, at most 1300 nm, or at most 1350 nm. Preferably, an emission can be a wavelength in the second near-infrared window of light (i.e. from 950-1400 nm).

In some embodiments, applying the imaging probe to the sample can include administering the imaging probe to a mammal. An imaging probe can be administered topically, enterally or parenterally. For example, an imaging probe can be swallowed, injected or inhaled. In some embodiments, a first binding partner configured to interact with a second binding partner inside a living mammal (i.e. in vivo).

In some embodiments, applying the imaging probe to the sample can include applying the imaging probe to a cell or tissue sample. In some embodiments, a first binding partner configured to interact with a second binding partner ex vivo.

In some embodiments, the targeting moiety can include *Escherichia coli*, which can express F-pili appendages. In some embodiments, the targeting moiety can include a biotin acceptor peptide. In some embodiments, the targeting moiety can include an anti-bacterial antibody, an M13, and a carbon nanotube. The anti-bacterial antibody can include an anti-*Staphylococcus aureus* antibody. In some embodiments, the targeting moiety can include a secreted protein, acidic and rich in cysteines (SPARC) binding peptide. The imaging probe can include a secreted protein, acidic and rich in cysteines (SPARC) binding peptide, an M13, and a carbon nanotube.

In some embodiments, the imaging probe can have a binding affinity for tumors located at various lengths in the body, for example, at depths of 9.7 to 18.2 millimeters. In some embodiments, the binding affinity of the imaging probe for a tumor can be different than the binding affinity of the imaging probe for healthy tissue.

In some embodiments, the imaging probe can be used for a surgery, such as for a cytoreductive surgery or for an ovarian cancer surgery. In some embodiments, the imaging probe can be used as an image guidance. The imaging probe can be used as an image guidance for a surgery. In some embodiments, a surgery using the imaging guidance can reveal a greater numbers of tumors from 1.3 millimeters to 3 millimeters as opposed to an unguided surgery.

In some embodiments, the imaging probe can have a fluorescence stability of at least 24 hours in vivo. The probe can be fluorescently stable across a 4 pH unit range from pH 4.5 to pH 8.5.

In some embodiments, the imaging probe is not cytotoxic to an ovarian cell line.

The imaging probe can be detected using new, customized imaging technology uniquely incorporating two laser sources and a two-axis stage controller designed to detect probes in three-dimensional space. This technology offers to determine accurate location and detect disease processes in but not only including, cells, animals and patients. The imaging probe and imager technology will provide important information about the behavior of systems including not only cells, animals, and patients. Other features or advantages will be apparent from the following detailed description of several embodiments, and also from the appended claims.

BRIEF DESCRIPTION OF THE DRAWINGS

(FIG. 4a) after applying a rigid image registration followed by a deformable image registration, and the change of PL intensity is represented as scaled colors (positive number in red indicates increase of PL intensity and the negative value in blue represents a decrease of PL intensity). PL intensity changes in other regions are attributed to the misalignment while registering the two mouse positions.

DETAILED DESCRIPTION

Figure 1:
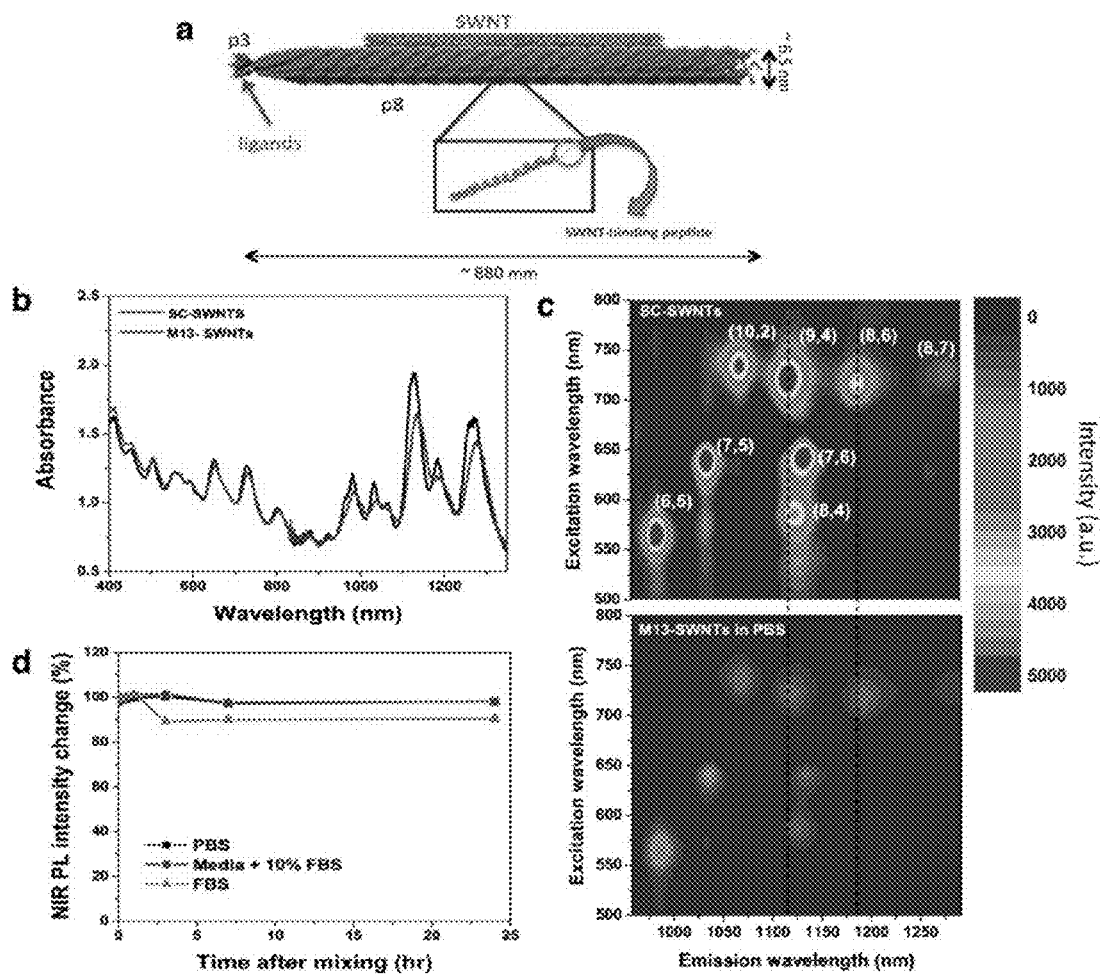
FIG. 1 illustrates a schematic of the imaging probe and its characteristics. a, M13-SWNT imaging probe: p8 is used to stably disperse SWNTs along the length of the virus, p3 is engineered for targeting with three different ligands, SPARC binding peptide (SBP), PSMA-antibody (anti-PSMA), and no-ligand. b, UV-vis-NIR absorption spectra and c, PL excitation (PLE) map of M13-SWNTs in phosphate-buffered saline (PBS) compared to SWNTs dispersed by 2 wt % sodium cholate (SC) in distilled water (denoted as SC-SWNTs). There is small red shifting of peaks. d, Serum stability test of M13-SWNTs. M13-SWNT is incubated in PBS, fetal bovine serum (FBS) and tissue culture media with 10% FBS, and PL intensity is measured to 24 h. HiPCO SWNTs are used for all studies.

Fluorescence imaging can be a powerful imaging modality for non-invasive and non-radiative detection of diseases and monitoring of treatment response. Weissleder, R.; Pittet, M. *Nature* 2008, 452, (7187), 580-589, which is incorporated by reference in its entirety. Second near-infrared (NIR) window light (950-1,400 nm) can be attractive for in vivo fluorescence imaging due to its greater penetration depth in tissues and low tissue autofluorescence compared to first NIR window light (650-950 nm). Smith, A. M.; Mancini, M. C.; Nie, S, *Nat Nanotechnol* 2009, 4, (11), 710-1, which is incorporated by reference in its entirety. Single-walled carbon nanotubes (SWNTs) can have great promise as in vivo fluorescence imaging agents due to their photoluminescence (PL) in the second NIR window and their interband transitions in the first NIR window (650-950 nm) can allow for excitation far from the emission line, further reducing background coming from excitation. SWNTs have previously been used for fluorescence imaging of live cells in vitro and whole animal in vivo. Welsher, K.; Liu, Z.; Daranciang, D.; Dai, H. *Nano Lett* 2008, 8, (2), 586-90, Leeuw, T. K.; Reith, R. M.; Simonette, R. A.; Harden, M. E.; Cherukuri, P.; Tsyboulski, D. A.; Beckingham, K. M.; Weisman, R. B. *Nano Lett* 2007, 7, (9), 2650-4, Welsher, K.; Liu, Z.; Sherlock, S. P.; Robinson, J. T.; Chen, Z.; Daranciang, D.; Dai, H. *Nat Nanotechnol* 2009, 4, (11), 773-80, each of which is incorporated by reference in its entirety. However, actively targeted, fluorescence imaging in vivo has not been achieved. This may be because it is challenging to achieve stable, biocompatible, and bright SWNTs with sufficient intensity for in vivo second NIR window fluorescence imaging due to the extremely hydrophobic surface of SWNTs and the sensitivity of the fluorescence to defect creation and bundle formation. For successful in vivo fluorescence imaging, the fluorescence intensity of SWNTs can be important as recently shown using SWNTs prepared by surfactant exchange with biocompatible phospholipid-polyethylene glycol (PL-PEG). Welsher, K.; Liu, Z.; Sherlock, S. P.; Robinson, J. T.; Chen, Z.; Daranciang, D.; Dai, H. *Nat Nanotechnol* 2009, 4, (11), 773-80, which is incorporated by reference in its entirety. Moreover, to further utilize the second NIR window fluorescence imaging for specific, accurate detection of targets such as malignant tumors and minimize non-specific uptake, coupling targeting functionality to brightly fluorescent SWNTs can be required. However, there has been no report on method or material system to obtain targeted SWNTs with bright enough fluorescence for in vivo imaging. He, X.; Gao, J.; Gambhir, S. S.; Cheng, Z. *Trends Mol Med* 2010, 16, (12), 574-83, which is incorporated by reference in its entirety.

Single-walled carbon nanotubes ("SWNTs"), which can be rolled cylinders of graphene, can have several advantages as potential imaging probe, for example, as part of targeted in vivo imaging probes. They can possess band-gap photoluminescence (PL) in the near infrared (nIR) and have not demonstrated a photo-bleaching threshold, thus permitting long exposure/integration times. (Hall, D. A., Ptacek, J. & Snyder, M. Protein microarray technology. *Mech Ageing Dev* 128, 161-167 (2007); Joos, T. Protein microarray technology. *Expert Rev Proteomic* 1, 1-3 (2004); Wolf-Yadlin, A., Sevecka, M. & MacBeath, G. Dissecting protein function and signaling using protein microarrays. *Curr Opin Chem Biol* 13, 398-405 (2009), each of which is incorporated by reference in its entirety). The photoemission can be sensitive to electron-donating or -withdrawing analytes or those that change the local dielectric constant, causing solvatochromism. (Stoevesandt, O., Taussig, M. J. & He, M. Y. Protein microarrays: high-throughput tools for proteomics. *Expert Rev Proteomic* 6, 145-157 (2009); Ramachandran, N. et al. Self-assembling protein microarrays. *Science* 305, 86-90 (2004); He, M. et al. Printing protein arrays from DNA arrays. *Nature Methods* 5, 175-177 (2008); Tao, S. C. & Zhu, H. Protein chip fabrication by capture of nascent polypeptides. *Nature Biotechnology* 24, 1253-1254 (2006); Chen, Z. et al. Protein microarrays with carbon nanotubes as multicolor Raman labels. *Nature Biotechnology* 26, 1285-1292 (2008); Hughes, R. C., Ricco, A. J., Butler, M. A. &

Martin, S. J. Chemical Microsensors. *Science* 254, 74-80 (1991); Lokate, A. M. C., Beusink, J. B., Besselink, G. A. J., Pruijn, G. J. M. & Schasfoort, R. B. M. Biomolecular interaction monitoring of autoantibodies by scanning surface plasmon resonance microarray imaging. *J Am Chem Soc* 129, 14013-14018 (2007), each of which is incorporated by reference in its entirety). While SWNT PL sensors have been developed for detecting β-D-glucose, DNA hybridization, divalent metal cations, assorted genotoxins, nitric oxide, pH and avidin, a targeted in vivo imaging probe. Using SWNT PL probes, the binding of molecules, which can quench the nanotube emission, can be detected even at the single molecule level. (Zheng, G. F., et al (2005); Thong, Z. H., Wang, D. L., Cui, Y., Bockrath, M. W. & Lieber, C. M. Nanowire crossbar arrays as address decoders for integrated nanosystems. *Science* 302, 1377-1379 (2003), each of which is incorporated by reference in its entirety). A nanotube can detect the stochastic fluctuations of single quenching molecules that adsorb or desorb in real time, which can allow the measurement of both forward and reverse binding rate constants, the ratio of which can be the inverse equilibrium or affinity constant.

An imaging probe can include a nanostructure and a targeting moiety (FIGS. 8a-8d). A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor. A nanostructure can be a carbon nanostructure. For example, a carbon nanostructure can be a nanotube, more specifically, a single walled nanotube.

A nanostructure can be a photoluminescent nanostructure, which can exhibit photoluminescence. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semiconductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. A property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure. A first binding partner can be a first molecule. A second binding partner can be a second molecule.

The association of a second binding partner with a first binding partner can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

In some embodiments, a viral protein or first binding partner can include a protein tag. A protein tag can be a peptide sequence grafted onto a protein, which can be used for separating (e.g. using tag affinity techniques), increasing solubility, immobilizing, localizing or detecting a protein. The protein tag can be a histidine tag, chitin binding protein tag, maltose binding protein tag, glutathione-S-transferase tag, c-myc tag, FLAG-tag, V5-tag or HA-tag. One method for creating a targeting moiety including a viral protein and a first binding partner is to bind the viral protein and the first binding partner. For example, one of the viral protein or first binding partner can include a protein tag, and the other can include a structure or domain that binds to the protein tag. Alternatively, a viral protein and a first binding protein can comprise a chimeric protein.

Binding of a first and a second binding partner can be selective binding, which can provide the selectivity needed to bind to the corresponding binding partner (or relatively small group of related molecules or proteins) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 µM, greater than 0.01 mM, or greater than 0.1 mM.

In some embodiments, binding of a first and a second binding partner can be specific binding. Specific binding can be more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 µM, less than 0.1 µM, or less than 0.01 µM. An analyte and a capture protein can bind with a dissociation constant greater than 1 nm, greater than 0.01 µM, greater than 0.1 µM, greater than 1 µM, greater than 0.01 mM, or greater than 0.1 mM.

The interaction of a first binding partner with a second binding partner can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between the first binding partner or viral protein and the nanostructure. As the distance between the nanostructure and the first binding partner or viral protein changes, a nanostructure property can also change. For example, nanostructure photoluminescence can also change.

The interaction of a first binding partner with a second binding partner can be reversible, meaning that the first binding partner can bind to the second binding partner and then release and be free of binding. The change in a property of the nanostructure due to the interaction of an first binding partner with a second binding partner can also be reversible. For example, the property of a nanostructure can have a first value, the first binding partner can bind to the second binding partner and alter the property to a second value, then the first binding partner can release from the second binding partner and the property can return to the first value.

The M13 bacteriophage is a filamentous virus that is approximately 900 nm in length and 6.5 nm in diameter. M13 bacteriophage contains about 2700 copies of a major coat protein, p8 protein, which are longitudinally assembled along the virus's DNA. The wild-type M13 virus coat includes about 2700 copies of major coat protein p8, which are stacked in units of five in a helical array. Moreover, several copies of minor coat proteins (p3, p6, p7, and p9 proteins) can be assembled at the two ends of the virus. This unique periodic, uniform structure is genetically controlled, and can be used to create tailor-made micro- or nanostructures. The various proteins may be genetically modified to have a specific peptide motif that can bind and organize nanomaterials, or bind to a first binding partner. Because the amino acid sequence of this motif is genetically linked to the virus DNA and contained within the virus capsid, exact genetic copies of the virus scaffold can be created easily and quickly reproduced by infection into bacterial hosts. In one embodiment, the major coat protein of M13 bacteriophage is genetically engineered to specifically bind to nanoparticles. Furthermore, the highly oriented helical major coat proteins of M13 virus promote the structural stability of individual virus-based nanotubes, and can increase the durability of devices or components incorporating them. Additional aspects of virus-templated formation of micro- and nanostructures are described in U.S. patent application Ser. No. 11/254,540, the contents of which are incorporated herein by reference.

As used herein, the term "peptide" denotes a string of at least two amino acids linked together by peptide bonds. Therefore, a peptide can also be a protein. Peptide may refer to an individual peptide or a collection of peptides. Peptides may contain only natural amino acids, although non-natural amino acids (e.g., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired activity of the peptide.

M13 bacteriophage can serve as a template for nanoparticle growth. See, for example, Ki Tae Nam, Dong-Wan Kim, P. J. Y. Science 2006, 312, 885, which is incorporated by reference in its entirety. Protein engineering techniques (e.g., phage display) can produce a virus that has a protein coat with binding affinity for a desired target material, e.g., an organic material such as carbon, a metal or a metal oxide. The protein coat protein can have a carbon or metal binding motif, which, for example, can be a negatively charged motif, e.g., tetraglutamate or a peptide with a binding affinity to a metal. For example, the motif can be a 12-amino acid peptide with a high affinity for Au. In one example, engineered M13 virus particles allowed control of the assembly of nanowires of $Co_3O_4$ with a small percentage of Au dopant. Id.

While M13 bacteriophage can have a major coat protein with a motif that binds specific metals, the motif can also block binding of other metals. For example, tetraglutamate can interact with various metal ions but blocks interaction with Au due to electrostatic repulsion. See, for example, Ki Tae Nam, Dong-Wan Kim, P. J. Y. Science 2006, 312, 885, which is incorporated by reference in its entirety. M13 bacteriophage can also be engineered to bind to different materials at different sites, by introducing different affinity motifs in the major and minor coat proteins.

Other viruses or biomolecules can be used in place of, or in addition to a selected virus such as the M13 virus. Alternatively or in addition, virus types which may be used for the inventive methods and compositions include, but are not limited to tobacco mosaic virus (TMV), cowpea mosaic virus, T7 bacteriophage, T4 bacteriophage, retrovirus, adenovirus, papillomavirus, parvovirus B 19, herpes simplex virus, varicella-zoster virus, cytomegalovirus, epstein-ban virus, smallpox virus, vaccinia virus, hepatitis B virus, polyoma virus, transfusion transmitted virus, enterovirus, corona virus, rhinovirus, hepatovirus, cardiovirus, aphthovirus, poliovirus, parechovirus, erbovirus, kobuvirus, teschovirus, coxsackie, reovirus, rotavirus, norwalk virus, hepatitis E virus, rubella virus, borna disease virus, dengue virus, hepatitis C virus, yellow fever virus, influenzavirus A, influenzavirus B, influenzavirus C, isavirus, thogotovirus, measles virus, mumps virus, respiratory syncytial virus, and their genetically engineered or altered versions. In various aspects, a portion of a selected virus can be genetically altered such that the altered portion provides a specific binding affinity for a material of interest.

As discussed above, M13 bacteriophage (or phage) is a versatile scaffold with five capsid proteins that can display material-specific peptides and/or targeting motifs through genetic engineering. In addition, its filamentous shape (length ~880 nm and diameter ~6.5 nm) can allow for multivalent interaction with one-dimensional materials such as SWNTs along the length of the phage, resulting in stable complexes (FIG. 1a). Huang, Y.; Chiang, C. Y.; Lee, S. K.; Gao, Y.; Hu, E. L.; De Yoreo, J.; Belcher, A. M. *Nano Letters* 2005, 5, (7), 1429-1434, Lee, Y. J.; Yi, H.; Kim, W. J.; Kang, K.; Yun, D. S.; Strano, M. S.; Ceder, G.; Belcher, A. M. *Science* 2009, 324, (5930), 1051-1055, Cwirla, S. E.; Peters, E. A.; Barrett, R. W.; Dower, W. J. *Proc Natl Acad Sci USA* 1990, 87, (16), 6378-82, each of which is incorporated by reference in its entirety. Recently, it was shown that M13 phage with pH sensitive SWNT-binding peptide expressed on the major coat proteins, p8, can effectively stabilize SWNTs in aqueous solution and be utilized for highly efficient electron collection in photovoltaic devices. Dang, X.; Yi, H.; Ham, M. H.; Qi, J.; Yun, D. S.; Ladewski, R.; Strano, M. S.; Hammond, P. T.; Belcher, A. M. *Nat Nanotechnol* 2011, which is incorporated by reference in its entirety. However, the possibility of SWNTs stabilized by M13 phage (designated as M13-SWNT) for biological applications has never been reported, and the capability to genetically control the multiple capsid proteins of M13 and spatially segregate their functionalities could be advantageous for constructing targeted and fluorescent imaging probe complexes which have been challenging to realize.

Second near-infrared (NIR) window light (950-1,400 nm) is attractive for in vivo fluorescence imaging due to its deep penetration depth in tissues and low tissue autofluorescence. Genetically engineered multifunctional M13 phage can assemble fluorescent single-walled carbon nanotubes (SWNTs) and ligands for targeted fluorescence imaging of tumors. M13-SWNT probe can be detectable in deep tissues even at a low dosage of 2 µg/mL and up to 2.5 cm in tissue-like phantoms. Moreover, targeted probes can show specific and up to four-fold improved uptake in prostate specific membrane antigen positive prostate tumors compared to control non-targeted probes. This M13 phage-based second NIR window fluorescence imaging probe has great potential for specific detection and therapy monitoring of hard-to-detect areas.

The imaging probe can be detected using an image detector including two laser sources to excite the target, a near-infrared detector for the monitoring the emission, and a stage for translating the target. Image data can be assembled by pulsing the lasers at the target, which independently excite the probe. The emission from the probe is detected by the NIR detector. The location of the emission can be mapped using the stage, such as a two-axis stage controller, to move the target. Alternatively, the lasers can be moved. The emission data can be collected to form three-dimensional image. The detector can be used to image cells, organisms or other structures.

Carbon Nanotube Imaging Probe as Bacterial Sensors

Bacterial infections are a cause of significant mortality and morbidity worldwide. In the US alone, in 2010, bacterial infections resulted in 40,000 deaths from sepsis and are also one of the major causes of limb amputations. Ning X. et al, *Nat Mater* 2011, 10, 602-607; Reiber G. E. et al, *Annals of Internal Medicine*, 1992, 117, 97-105, each of which is incorporated by reference in its entirety. In spite of the availability of antibiotics, a major limitation in the effective treatment of bacterial infections is an inability to image then in vivo with accuracy and sensitivity. As a result, in most cases bacterial infections are diagnosed only after they have become systemic metastasized infections, having caused significant tissue damage; at which they are challenging to treat. Further, the increasing development of bacterial resistance to antibiotics has reached alarming proportions, and thus necessitates need for imaging tools to facilitate early detection and treatment of bacterial infections. In the US alone, the economic impact of antibiotic-resistant bacterial infections is estimated to be between $5 billion and $24 billion per year. Hall B. G., *Nat Rev Micro* 2004, 2, 430-435, which is incorporated by reference in its entirety.

Optical imaging of bacteria in vivo is much less developed than other methods such as radioimaging and MRI, due to lack of availability of target-specific molecular probes and the associated instrumentation required for imaging infections in deep tissue. In fact, ex vivo labeled autologous leukocytes were developed in the 1970s and 1980s, and are still considered the "gold standard" nuclear medicine technique for infection and inflammation imaging. $^{111}$In or $^{99m}$Tc-labeled leukocytes have been shown to have a diagnostic accuracy ~90% for both acute and chronic infections. Rennen H. J. et al, *Eur J Nucl Med* 2001, 28, 241-252, which is incorporated by reference in its entirety. Another interesting chemistry approach has been used by Bettegowda, C. et al. that relies on the phosphorylation and trapping of the thymidine kinase substrate 1-(2'-deoxy-2'-fluoro-β-D-arabinofuranosyl)-5-iodouracil ([$^{125}$I]FIAU) for bacteriolytic therapy of tumors. Bettegowda C. et al, *Proc Natl Acad Sci USA* 2005, 102, 1145-1150, which is incorporated by reference in its entirety. However, these radiopharmaceutical methods are based on γ-counting radiograms, and expose the patient to radiation hazard, and underscore the need for pure optical imaging technologies. Moreover, they are laborious to design and implement, and require specialized equipment and operator training.

One approach to optical imaging of bacterial infections in vivo was using genetic reporter systems such as light-emitting luciferase enzymes, or green fluorescent protein (GFP), with notable success. The work on bacterial imaging in living hosts, by Contag, C. H. et al., demonstrated the detection of virulent *Salmonella* strains transformed with a plasmid conferring constitutive expression of bacterial luciferase. Contag C. H. et al, *Molecular Microbiology* 1995, 18, 593-603, which is incorporated by reference in its entirety. The spatio-temporal evolution of the course of the infection can be monitored under varied antibiotic treatment conditions. Although this method has a significant advantage of the absence of bioluminescent autofluorescence background from normal mammalian tissue, its other major problems are overwhelming. First, oxygen is an essential substrate for the luciferase reaction, and only bacteria present in oxygenated microenvironments will show bioluminescence. This may lead to false negative results. Second, and perhaps more importantly, pathogenic bacteria in their native environments do not express endogenous optical reporters such as luciferase or GFP, and as such this is an artificial construct with limited application in clinical practice.

Developing bacterial targeting probes with exogenous contrast agents for optical imaging is needed. One component can be the bacteria targeting group, and several studies have employed antibodies, lectins, sugars, antibiotic drugs, enzyme substrates and antimicrobial peptides as affinity ligands. Leevy W. M. et al, *J. Am. Chem. Soc.* 2006, 128, 16476-16477, which is incorporated by reference in its entirety. One technique uses cationic molecules that are electrostatically attracted to the negatively charged anionic phospholipids in the membranes of bacterial cells. The anionic surfaces of bacteria are different from most healthy mammalian cells, whose cell membranes contain mainly zwitterionic phospholipids with a neutral charge profile. Boon J. M. et al, *Medicinal Research Reviews* 2002, 22, 251-281, which is incorporated by reference in its entirety. In spite of this, one major limitation of using generic cationic peptides as a targeting agent is their tendency to penetrate and get retained by mammalian cells, resulting in poor specificity in imaging, compared to antibody-based approaches. Nekhotiaeva N. et al, *The FASEB Journal* 2004, 18, 394-396; Bullok K. E. et al, *Mol Imaging* 2006, 5, 1-15, each of which is incorporated by reference in its entirety. Similarly, antimicrobial peptides suffer from a poor signal-to-background noise ratio, since they effect degradation of the bacterial cell membrane target and result in diffuse signal spread. Lupetti A. et al, *European Journal of Nuclear Medicine and Molecular Imaging*, 2002, 29, 671-679; Welling M. M. et al, *Eur J Nucl Med* 2000, 27, 292-301, each of which is incorporated by reference in its entirety. This problem of nonspecificity has been addressed to a certain extent by engineering novel compounds, such as a cationic bis-dipicolylamine-Zinc(II) affinity group conjugated with a NIR carbocyanine fluorophore, developed by Leevy, W. M. et al. Leevy W. M. et al, *J. Am. Chem. Soc.* 2006, 128, 16476-16477; Leevy W. M. et al, *Bioconjugate Chem.* 2008, 19, 686-692, each of which is incorporated by reference in its entirety. Using this probe, they were able to selectively image *S. aureus* and *E. coli* infections in mice, even in the presence of human endothelial cells. However, there are still doubts concerning its specificity, due to the possibility of the ligand targeting the adjacent necrotic tissue produced by the infection. In contrast, probes based on antibody-mediated targeting are a popular choice because they can bind tightly to specific molecular targets on the surfaces of both Gram-positive and Gram-negative bacteria.

A special class of maltodextrin-based imaging probes was reported by Ning, X. et al. Ning X. et al, *Nat Mater* 2011, 10, 602-607, which is incorporated by reference in its entirety. These complexes are composed of a fluorescent dye molecule conjugated to maltohexaose, which are internalized into the bacterial cytoplasm through the bacteria-specific maltodextrin transport pathway. The authors were able to use these probes for imaging different strains such as *E. coli, S. aureus, Pseudomonas aeruginosa* and *Bacillus subtilis*, and are able to clearly detect bacteria in vivo with a high specificity over lipopolysaccharide-induced inflammation, and inflammation induced by LamB-negative or metabolically inactive bacteria. While this is certainly a promising candidate for imaging bacterial infections, the key challenges still remain: the ability to image bacterial colonies in deep tissue, accurately for small infections is limited due to the use of small molecule NIR dyes with low Stokes' shift, hence significant background noise. This defines the need for developing such a technique.

Optical fluorescence imaging in the second-window near-infrared (NIR-II) wavelength domain emergs as a promising technique, fueled by the development of better molecular probes, effective targeting agents and custom-built imagers. Liu Z. et al, *Nano Research* 2010, 2, 85-120; Yi H. et al, *Nano Lett.* 2012, 12, 1176-1183; Welsher K. et al, *Proc Natl Acad Sci USA* 2011, 108, 8943, each of which is incorporated by reference in its entirety. Near IR (700 to 2500 nm) light can penetrate biological tissue more efficiently than visible light. Traditional NIR probes in the biological transparency window near 800 nm (NIR-I) such as indocyanine green and semiconductor quantum dots outperform short-wavelength emitting dyes; however they still suffer from poor penetration depth due to large scattering of the emitted signal by tissue. The consensus is that the penetration depth can be maximized at wavelengths between 1 and 1.4 µm (NIR-II), with a signal-to-noise ratio that may be 100-fold higher than NIR-I. Bashkatov A. N. et al, *J. Phys. D: Appl. Phys.* 2005, 38, 2543-2555; Tamara L. T. et al, *Journal of Biomedical Optics* 2001, 6, 167-176; Lim Y. T., *Molecular Imaging* 2003, 2, 50-64, each of which is incorporated by reference in its entirety.

Carbon nanotubes, functionalized and tuned appropriately, can be used to detect, identify, image and monitor bacterial infections. Biocompatible Single-Wall carbon NanoTubes (SWNTs) are an attractive candidate for use as fluorophores in NIR-II imaging, due to their photoluminescence in the 1.1-1.4 µm range, large Stokes' shift between excitation and emission, ultralow autofluorescence background, relative insensitivity to photobleaching compared to organic dyes, ability to be functionalized with targeting/drug delivery agents, and high optical absorbance in NIR-I offering the additional possibility of photothermal therapy. As grown, bare CNTs are highly hydrophobic, and not soluble in aqueous media. For biomedical applications, surface functionalization is required to solubilize the CNTs and render them biocompatible and low toxicity.

A method of using carbon nanotubes as bacteria sensors can be developed. M13 bacteriophage as a versatile, multifunctional scaffold can also be used. This vector can act as a biological surfactant for dispersing carbon nanotubes in aqueous medium, forming an M13-SWNT complex. M13-SWNT retains the desired optical properties of SWNTs for imaging applications. M13-SWNT can target and locate pathogenic infections of *E. coli* in living hosts.

Further, a 1-step tuning process can tune this M13-SWNT complex suitable to detect other strains of bacteria, which do not express F-pili. By genetically engineering the p3 coat protein of M13 to express a biotin acceptor peptide (BAP-M13-SWNT), the biotin protein can be attached on the p3. This generic biotin-M13-SWNT construct can be used against virtually any strain of bacteria for which an anti-bacterial antibody is available. Once a suitable antibody is identified, it is conjugated with streptavidin. Through a one-step reaction between the streptavidin-coated antibody and the biotin expressed on the p3 of M13, a probe (anti-bacterial antibody-M13-SWNT) can be created. Anti-*S. aureus*-M13-SWNT probe can target and locate pathogenic infections of *S. aureus* in living hosts.

Once localized, the anti-bacterial antibody-M13-SWNT can be used as an optical imaging probe for NIR-II fluorescence imaging of the bacterial infection. Optical imaging using NIR-II fluorescence of carbon nanotubes makes it possible for sensing, detecting, imaging, selectively identifying, locating and noninvasively monitoring the pathogen in living hosts.

Carbon Nanotube Imaging Probe as Surgical Guidance

Imaging modalities including computed tomography (CT), magnetic resonance imaging (MRI), ultrasound (US) and positron emission tomography (PET) are used widely in oncology for non-invasive diagnosis, tumor staging, monitoring response to therapy, and detecting recurrent or residual disease. Current imaging modalities including CT, MRI and US can provide important anatomical information about the size and location of tumors. However, anatomical-based imaging modalities are best suited to resolve tumors greater than 1 cm in diameter ($>10^9$ cells), and these modalities have additional drawbacks including high cost, low portability, hazardous radiation exposure, and limited specificity and spatial resolution. Weissleder R., Science 2006, 312, 1168, which is incorporated by reference in its entirety. For ovarian cancer, detection of early-stage tumors correlates with greater than 90% five-year survival rates. Etzioni R. et al., Nat Rev Cancer 2003, 3, 243, which is incorporated by reference in its entirety. Towards this end, molecular imaging represents an attractive option to visualize processes involving nucleic acids, enzymatic activity in tumors, or secreted extracellular proteins involved in the early stages of tumorigenesis before purely anatomical detection is feasible. These molecular-scale processes can be visualized by optical fluorescence imaging, which offers a comparatively low cost, portable, and safe method with the ability for real-time imaging, superior resolution, and high specificity for detection of small tumor nodules in both pre-operative tumor staging and intraoperative image-guided surgery. Weissleder R. et al, Nature 2008, 452, 580; Urano Y. et al., Sci Transl Med 2011, 3, 110, each of which is incorporated by reference in its entirety. While recent work has focused on using visible and near-infrared (650 nm-900 nm) wavelength fluorescent dyes as contrast agents for delineating tumor margins in both pre-clinical cancer models and human clinical trials, these agents are suboptimal for non-invasive, reflectance-based imaging due to limited penetration depth (3-5 mm) and high tissue autofluorescence. Urano Y. et al., Sci Transl Med 2011, 3, 110; Nguyen Q. T. et al., Proc Natl Acad Sci USA 2010, 107, 4317; van Dam G. M. et al., Nat Med 2011, 17, 1315, each of which is incorporated by reference in its entirety. During intraoperative surgery, these dyes may additionally undergo photobleaching, thereby reducing the ability of the surgeon to locate and resect tumors.

Single-walled carbon nanotubes (SWNTs) hold great promise as fluorescence imaging agents due to the large interband difference between their excitation and emission wavelengths, resulting in minimal spectral overlap and tissue autofluorescence. In particular, the minimal tissue autofluorescence observed with SWNTs greatly enhances target-to-background ratios necessary for improved detection of small tumor nodules in confined anatomic regions. SWNT emission at longer wavelengths in the near-infrared second optical window (NIR2: 950-1400 nm) results in less optical scattering and deeper tissue penetration compared to shorter wavelength visible and near-infrared imaging agents. In addition, unlike visible and near-infrared dyes, well-functionalized SWNTs are less susceptible to photobleaching or quenching effects, which make them attractive for continuous and longer-term imaging required during surgical planning and resection. Heller D. A. et al., J Am Chem Soc 2004, 126, 14567, which is incorporated by reference in its entirety. M13 bacteriophage-stabilized SWNTs can target subcutaneous prostate tumors in pre-clinical models for fluorescence imaging in the second optical window. Yi H. et al., Nano Lett 2012, 12, 1176, which is incorporated by reference in its entirety. SWNTs have also been utilized for vascular and deep tissue fluorescence imaging. Welsher K. et al., Nat Nanotechnol 2009, 4, 773; Welsher K. et al, Proc Natl Acad Sci USA 2011, 108, 8943, each of which is incorporated by reference in its entirety. To date, however, there has been no report of a molecularly-targeted, second optical window imaging agent for non-invasive imaging to assist the surgical removal of tumors and tumor margins.

A molecularly targeted SWNT probe can selectively localize to SPARC (Secreted Protein, Acidic and Rich in Cysteines)—expressing tumor nodules in an orthotopic mouse model of human ovarian cancer. Ovarian cancer remains a major health care problem for women. Annually, 225,000 women worldwide are diagnosed with epithelial ovarian cancer (EOC) and approximately 140,000 women die from it. Jemal A. et al., CA: a cancer journal for clinicians 2011, 61, 69, which is incorporated by reference in its entirety. While women with early stage ovarian cancer (FIGO stage I/II) can be cured, advanced stage ovarian cancer (FIGO III/IV) remains considerably more difficult to treat. Unfortunately, eighty percent of women with EOC have metastatic disease at the time of diagnosis, and many undergo a treatment regimen of surgery and chemotherapy. The study focused on ovarian cancer because clinical evidence indicates that optimal cytoreductive surgery can significantly prolong the median overall survival of patients as well as reduce disease morbidity. Chi D. S. et al., Gynecologic oncology 2006, 103, 559, which is incorporated by reference in its entirety. Using the long wavelength emission of these second optical window probes, the detection limit of labeled tumors and their target-to-background ratios was determined. Taking advantage of the unique optical properties of SWNTs, this probe can assist the surgeon in identifying and resecting smaller ovarian tumors during cytoreductive surgery. Molecularly-targeted, second optical window fluorescence probes have potential clinical utility for non-invasive surgical planning and intraoperative image guidance for patients with ovarian and other types of cancer.

A single fluorescence imaging agent can be developed and used for high contrast, non-invasive detection and guidance for cytoreduction of disseminated ovarian tumors. These targeted, M13-stabilized SWNT probes can assist surgical removal of ovarian tumors with excellent sensitivity as confirmed by subsequent pathological examination. The probe is sensitive for identifying tumor nodules located on several abdominal viscera, the peritoneal wall, and the bowel mesentery. Compared to fluorescent probes in the visible or near infrared regimes, the fluorescence of SWNTs is not limited by quenching, allowing for long-term, continuous imaging. With the development of advanced imaging platforms, surgeons will be able to visualize tumors both before and throughout surgical procedures, thereby significantly improving fluorescence-guided tumor resection. Cytoreductive surgery accompanied by image guidance leads to identification and removal of smaller tumor nodules. While NIR2 images could not provide three-dimensional localization of the tumor implants, they provided information about the sites of disease burden requiring closer surgical examination. Imaging of regions in which the surgeon was initially reluctant to explore in an effort to minimize morbidity such as excessive blood loss, but later revealed a positive NIR2 signal, often led to the identification and excision of additional tumor nodules missed on non-image guided approaches. The majority of clinical evidence suggests that optimal cytoreductive surgery, currently defined as the removal of tumors with diameters of 1 cm or larger, is correlated with improved overall survival rates. Chi D. S. et al., *Gynecologic oncology* 2006, 103, 559, which is incorporated by reference in its entirety. SWNT-based molecular probes could greatly aid in surgical planning and cytoreduction in order to help achieve a reduction in mortality rates in the future.

Sub-millimeter tumors can be detected with excellent target-to-background ratios using M13-stabilized SWNTs, in part due to properties of the particles that lead to low tissue scattering and minimal tissue autofluorescence in the second optical window. In comparing excised tumors with unaffected intestinal tissues as a background measurement, high TBRs of ~112 using the SPARC-targeted M13-SWNT probes can be observed. Following intraperitoneal administration, some uptake is observed using non-targeted SWNT probes, which is most likely due to non-specific binding interactions or convective flow patterns present within the peritoneal cavity. Fluorescence imaging in the second optical window offers the promise of imaging at greater penetration depths (>3-5 mm) with reduced optical scattering within the tissue. Using a reflectance imaging system, 1 mm diameter tumors up to a maximal depth between 9.7 and 18.2 mm can be detected. This is higher than previous reports that detected mammary tumors labeled with activatable Cy5 probes. Nguyen Q. T. et al., *Proc Natl Acad Sci USA* 2010, 107, 4317, which is incorporated by reference in its entirety. Future work to enhance the fluorescence of M13-SWNTs using plasmonic nanomaterials and molecular targeting using other ligand-receptor interactions including the folate receptor may offer further improvements on current limits of detection and resolution. van Dam G. M. et al., *Nat Med* 2011, 17, 1315; Hong G. S. et al., *J Am Chem Soc* 2010, 132, 15920, each of which is incorporated by reference in its entirety. These longer wavelength emitting probes will greatly aid in locating ovarian tumors confined to deep anatomical regions.

SBP-M13-SWNTs injected intraperitoneally co-localized with stromal SPARC expression on the periphery of the ovarian tumor nodules. Tumor nodules labeled with the probes exhibited high signal with low background in the surrounding healthy tissues, including liver, spleen, and intestine. These high organ-specific TBRs in part assisted with more accurate surgical resection of tumor nodules localized to the organ surfaces. Because the probes can visualize the tumor margins, they have potential to assist the surgeon in delineating tumors from healthy tissue for improved resection of other solid tumors, as also demonstrated by approaches using activatable peptides and dyes, fluorescein conjugates, and multimodal nanoparticles. Urano Y. et al., *Sci Transl Med* 2011, 3, 110; Nguyen Q. T. et al., *Proc Natl Acad Sci USA* 2010, 107, 4317; van Dam G. M. et al., *Nat Med* 2011, 17, 1315; Olson E. S. et al., *Proc Natl Acad Sci USA* 2010, 107, 4311; Kircher M. F. et al., *Nat Med* 2012, 18, 829, each of which is incorporated by reference in its entirety.

M13-SWNT molecular probes exhibit long-term stability and fluorescence for at least 24 hours for in vivo imaging applications. Since the probe retains its optical properties under various pH and physiological environments and under constant excitation, it is an attractive candidate for long-term imaging for non-invasive detection and fluorescence-guided surgery. The safety of M13 in the clinic has been shown in a Phase I clinical trial to identify patient-specific ligands. The virus possessed a low toxicity profile, elicited a "sub-maximal" humoral immune response, and patients demonstrated no adverse allergic responses. Krag D. N. et al., *Cancer Res* 2006, 66, 7724, which is incorporated by reference in its entirety. Similarly, recent work has confirmed the non-cytotoxicity of well-functionalized, short length SWNTs administered in vivo through histology and serum chemistry. Kolosnjaj-Tabi J. et al., *ACS Nano* 2010, 4, 1481; Liu Z. et al., *Proc Natl Acad Sci USA* 2008, 105, 1410; Schipper M. L. et al., *Nat Nanotechnol* 2008, 3, 216, each of which is incorporated by reference in its entirety. These initial findings support the potential use of these nanomaterials in a clinical setting.

While SWNTs can be used for fluorescence imaging, others have demonstrated their utility as carriers for therapeutic cargoes or genes as well as photothermal ablative therapy. Liu Z. et al, *Nano Res* 2009, 2, 85; Kam N. W. et al, *Proc Natl Acad Sci USA* 2005, 102, 11600; Burke A. et al., *Proc Natl Acad Sci USA* 2009, 106, 12897, each of which is incorporated by reference in its entirety. SBP-M13-SWNTs for in vivo heating of the local tumor microenvironment can potentially be used as sensitizing agents to chemotherapeutic agents and multimodal imaging and therapeutic agents.

Highly sensitive, non-invasive detection of small, deep tumors remains a challenge for conventional imaging modalities. Tumor staging, surgical procedures, and monitoring response to therapy stand to benefit greatly from such technological advances. A targeted nanomaterial containing SWNTs can be used to non-invasively visualize disseminated ovarian tumor nodules in the peritoneal cavity. This probe displays a higher affinity for tumor nodules in comparison to normal abdominal organs by calculating tissue-specific tumor-to-background ratios. Additionally, cytoreductive surgery—a procedure in which the amount of residual disease correlates with ovarian cancer patient survival—can be improved with SWNT image guidance, and when performed by a gynecologic oncologist, can lead to the identification of sub-millimeter tumor nodules in an orthotopic mouse model. Thus, targeted SWNTs can be used for non-invasive cancer imaging, which highlights a potential clinical role in providing surgical guidance for tumors not immediately visible to the naked eye.

To advance the findings closer to clinical translation, new instrumentation will be required to allow for intraoperative surgical guidance in real-time, and three-dimensional tomography for quantitative analysis and more accurate localization of tumors. Simulations suggest that at near-infrared wavelengths that define the second optical window, SWNT-based probes may be detectable at depths up to 10 cm on improved imaging platforms, highlighting the potential utility of these particles in human subjects. Kim S. et al., *Nat Biotechnol* 2004, 22, 93, which is incorporated by reference in its entirety. This new platform would allow for real-time, non-invasive imaging and processing for accurate visualization of tumors during tumor staging, pre-surgical planning, and during cytoreductive procedures. Coupling improved instrumentation with probe development will greatly improve the ability to detect tumors at earlier stages and possibly detect micrometastases. The ability to detect tumors of smaller sizes at earlier time points may also provide fundamental insights into tumorigenesis and disease progression, as well as allow clinicians to better monitor therapeutic responses and recurrence of disease. The modular nature of the M13 platform, which can incorporate patient-specific targeting peptides or antibodies, will enable the development of 'personalized imaging' tailored to the unique tumor microenvironments present within individual patients.

Materials and Methods

M13 Phage-SWNTs Complexation

To prepare the starting SWNTs solution, as-produced and non-acid treated HiPCO single-walled carbon nanotubes, purchased from Unidym, were diluted in a 2 wt % sodium cholate (SC) aqueous solution. The diluted solution was homogenized for 1 h, cup-horn sonicated for 10 min at 90% amplitude and then centrifugated at 30,000 rpm for 4 h to get individually dispersed SWNT. SWNT concentration was calculated using the extinction coefficient of HiPCO SWNT at 632 nm, $\varepsilon_{632\ nm}$=0.036 L/mg·cm (or $A_{632@1\ cm} \times 27.8$=[SWNTs] in µg/mL). For the complexation, a phage-to-SWNT ratio of 1:1 was used. The complexation was done according to previously reported method. Dang, X.; Yi, H.; Ham, M. H.; Qi, J.; Yun, D. S.; Ladewski, R.; Strano, M. S.; Hammond, P. T.; Belcher, A. M. Nat Nanotechnol 2011, which is incorporated by reference in its entirety. Briefly, calculated amount of SWNT-binding phage solution was mixed with the calculated volume of SWNTs dispersed by 2 wt % SC in water. The mixed solution was dialyzed against water (10 mM NaCl, pH=5.3, which is pI of SWNT-binding phage) for two days with frequent solution changes, and the pH of the dialyzing solution was increased to 10 after two days of dialysis. A dialysis membrane with MWCO of 12,000-14,000 (SpectraLabs) was used for the dialysis. After the complexation, concentrated PBS (10×PBS) was added to the complexes, and the complex solution was vortexed and centrifuged at 6,000 rpm for 5 min.

In a different method, the calculated amount of SWNT-binding phage solution was mixed with the calculated volume of SWNTs dispersed by 2 wt % SC in water to achieve a 1:1 stoichiometric ratio of phage-to-SWNT. The solution was placed in a dialysis membrane with MWCO 12,000-14,000 and dialyzed against water (10 mM NaCl, pH=5.3) for 48 hours with frequent solution changes. pH of the dialyzing solution was increased to 10 after two days of dialysis. After dialysis, the virus-SWNT complex was removed and placed in a conical tube. Prior to experiments, samples were resuspended in 1×PBS, vortexed and centrifuged at 6000 rpm for 5 min.

Another Method of Functionalizing Carbon Nanotubes

As grown, bare SWNTs are highly hydrophobic, insoluble in aqueous media. Numerous functionalization approaches such as covalent functionalization (oxidation, PEGylation, cycloaddition), noncovalent bonding (amphiphilic surfactants like PEGylated phospholipids, pyrene derivatives, proteins), can have varying degrees of success, without compromising the optical properties of SWNTs. Liu Z. et al, Nano Research 2010, 2, 85-120, which is incorporated by reference in its entirety. For biomedical applications, surface functionalization is required to render them biocompatible. It also helps to make the surface hydrophilic in order to disperse them in aqueous suspension for suitable biological applications.

Figure 9:
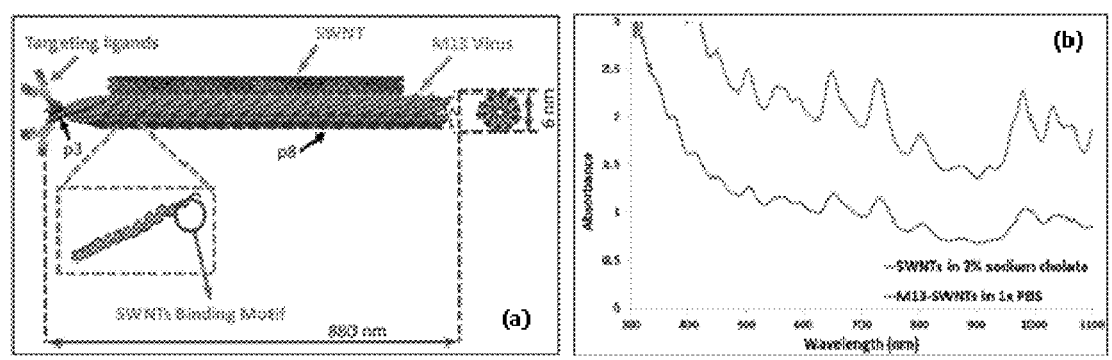
FIG. 9(a) illustrates the schematic of the structure of the M13 filamentous bacteriophage, rendered in purple. Typical dimensions are ~880 nm in length and ~6 nm in diameter. Of interest shown here is the major coat protein, p8, which forms a multi-copy π-π binding interaction with SWNTs. At one end is the minor coat protein, p3, which can be used to conjugate targeting ligands such as antibodies.
FIG. 9(b) shows absorbance spectra of SWNTs dispersed in an aqueous solution of 2 wt. % sodium cholate, an organic surfactant (blue curve) and M13-SWNT (red curve). It is observed that the general characteristics of the SWNT peaks are maintained after surfactant exchange with M13. There is slight red shift observed in the M13-SWNT spectra.

M13 bacteriophage can be used as a biological surfactant for carbon nanotubes. Dang X. et al, Nature Nanotechnology 2011, 6, 377-384, which is incorporated by reference in its entirety. M13 is a long filamentous virus with a length ~880 nm and a diameter ~6 nm. This aspect ratio is quite similar to SWNTs, and M13 is therefore naturally suited to be used as a scaffold for SWNTs. FIG. 9(a) shows the typical structure of M13-functionalized SWNT. There are five capsid proteins on the surface of the virus, which can be genetically engineered to express specific peptides or targeting ligands. The major coat protein p8 can be modified to express a pH-sensitive SWNT-binding peptide, expressed in all 2700 copies of p8. This peptide forms a multivalent, high-copy π-π interaction with the SWNT aligned longitudinally along the length of the virus. In addition, there are 5 copies of the minor coat protein p3 of the M13 virus, which are also accessible to modification for attaching other targeting moieties. This capability can create a one-step tuning process for targeting various strains of bacteria.

The procedure for complexing SWNTs with the M13 virus has been established. Dang X. et al, Nature Nanotechnology 2011, 6, 377-384, which is incorporated by reference in its entirety. Briefly, as-synthesized, non acid-functionalized HiPCO SWNTs, length <1 µm and diameter ~1 nm (NanoIntegris, Calif., USA) are dispersed in 2 wt. % sodium cholate (SC) (Sigma-Aldrich, MO, USA) solution, cup-horn sonicated for 10 minutes and centrifuged at 30,000 rpm for 4 hr. to get well-dispersed SWNTs (SC-SWNT). The final SWNT concentration of the supernatant is calculated using Beer-Lambert's Law where the extinction coefficient of HiPCO SWNT at 632 nm, $A_{632\ nm}$=0.036 L/mg·cm (or absorbance for 1 cm path length at 632 nm, $A_{632@1\ cm} \times 27.8$=[SWNTs] in µg/ml). FIG. 9(b) shows the absorbance spectra of the SC-SWNT (blue curve) as a function of wavelength, giving a calculated value of [SWNTs]=58.46 µg/mL. For the complexation with M13, SC-SWNTs are be mixed with phage at a 1:1 ratio and dialyzed extensively by increasing pH gradients. After the complexation, the M13-SWNT complex is adjusted to 1×PBS. The absorbance spectra of M13-SWNT is shown in FIG. 9b (red curve), giving a calculated value of [SWNTs]=28.64 µg/mL. It is observed that after complexation, M13-SWNT shows the same qualitative peak characteristics as the organic surfactant-dispersed SC-SWNTs. There is slight red shifting of the M13-SWNT peaks, which may be attributed to the different dielectric environment surrounding the SWNTs when they are bound by sodium cholate molecules, compared to binding with M13, or due to potentially small amount of bundling of the SWNTs during the complexation process.

Absorption Spectroscopy and NIR Photoluminescence Excitation (PLE) Mapping

Absorption measurements were taken with a Shimadzu UV-3101 PC UV-VIS-NIR Scanning Spectrophotometer. PL from SWNT was measured with a home-built near-infrared (NIR) PL microscope. An inverted microscope was coupled to OMA V 1D InGaAs array detector (Princeton Instruments) through Acton SP2500 spectrometer (Princeton Instruments). For three-dimensional profile, a Xe lamp coupled to a monochromator was used as excitation source.

Alternatively, Absorption measurements were taken with a DU800 spectrophotometer (Beckman Coulter). PL of SWNT was measured with a FluoroMax spectrofluorometer (Horiba Jobin Yvon).

Genetic Engineering of SPARC Binding Peptide (SBP) onto p3 of SWNT-Binding M13 Phage SPARC binding peptide (designated as SBP), SPPT-GINGGG, was used for specific binding to SPARC. Oligonucleotides encoding SBP, 5'(Phos)-GTA CCT TTC TAT TCT CAC TCT TCA CCA CCG ACT GGA ATT AAC GGA GGC GGG TC-3' and 5'(Phos)-GGC CGA CCC GCC TCC GTT AAT TCC AGT CGG TGG TGA AGA GTG AGA ATA GAA AG-3' (IDT) were annealed to form a DNA duplex. Kelly, K. A.; Waterman, P.; Weissleder, R. Neoplasia 2006, 8, (12), 1011-1018, which is incorporated by reference in its entirety. The M13-based cloning vector was isolated from the SWNT-binding phage (designated as DSPH) using standard miniprep kit (QIAGEN). DNA was digested with Eag I and Acc65 I restriction enzymes, dephosphorylated and agarose-gel purified. Purified vector and DNA duplex were ligated using T4 DNA ligase at 16° C. overnight and transformed in electrocompetent XL-1 Blue cells (Stratagene). Transformed cells were incubated for 1 h and plated in top agar and incubated at 37° C. overnight. Blue plaques were amplified, and isolated DNA was purified and sequenced to confirm the insertion of oligonucleotides to express SBP on p3.

In a different method, oligonucleotides encoding SPARC binding peptide (designated as SBP, SPPTGINGGG[26]), 5'(Phos)-GTA CCT TTC TAT TCT CAC TCT TCA CCA CCG ACT GGA ATT AAC GGA GGC GGG TC-3' and 5'(Phos)-GGC CGA CCC GCC TCC GTT AAT TCC AGT CGG TGG TGA AGA GTG AGA ATA GAA AG-3' (IDT) were annealed and inserted into the EagI and Acc65I restriction endonuclease sites of double stranded M13 DNA for N-terminal display on p3. The M13-based cloning vector was isolated from the SWNT-binding phage using standard DNA isolation (QIAGEN). Ligations were transformed in electrocompetent XL-1 Blue cells (Agilent Technologies), plated in top agar and incubated at 37° C. overnight. DNA was purified (Qiagen) from isolated blue plaques and sequenced to confirm the insertion of SBP on p3.

Genetic Engineering for Biotin-Accepting Peptide (BAP) onto p3 of SWNT-Binding M13 Phage The genetic engineering of BAP is identical to the cloning of SBP described above, except that oligonucleotides sequences, 5'(Phos) GTA CCT TTC TAT TCT CAC TCT GGC CTG AAC GAC ATC TTC GAG GCT CAG AAA ATC GAA TGG CAC GAG TC 3' and 5'(Phos) GGC CGA CTC GTG CCA TTC GAT TTT CTG AGC CTC GAA GAT GTC GTT CAG GCC AGA GTG AGA ATA GAA AG 3', were used to make a DNA duplex encoding BAP. Beckett, D.; Kovaleva, E.; Schatz, P. J. Protein Sci 1999, 8, (4), 921-9, which is incorporated by reference in its entirety.

Cell Lines and Culture

DU145 human prostate carcinoma cell line was provided courtesy of Dr. Kimberly Kelly (University of Virginia). LNCaP human prostate carcinoma cell line was purchased from ATCC. DU145 was grown in Dulbecco's Minimum Essential Medium (DMEM, Hyclone) supplemented with 10% fetal bovine serum (FBS) (Hyclone) and 1% penicillin/streptomycin (Invitrogen) at 37° C. in 5% $CO_2$. LNCaP were grown in phenol red-free RPMI medium (Hyclone), supplemented with 10% FBS, 1% penicillin/streptomycin, 1% sodium pyruvate (Invitrogen), and 1% HEPES buffer (Invitrogen) 37° C. in 5% $CO_2$.

Flow Cytometry

To determine SPARC expression, DU145 and LNCaP cells were harvested. 1,000,000 cells/sample were incubated with complete media and spun at 1,200 rpm for 5 min. After centrifugation, samples were washed two times with PBS and fixed with cold 4% paraformaldehyde for 10 min at room temperature. After two washes, cells were washed with 0.2% saponin in PBS (SAP) for 10 min. Cells were centrifuged at 1,200 rpm for 5 min. Cells were then incubated with 1:20 mouse isotype (abcam) or anti-human SPARC-phycoerthrin (PE) (R&D Systems) in SAP buffer. After washes, samples were run on FACScan (Becton Dickinson) and gated for 10,000 events. Samples were run in triplicate. For PSMA expression, DU145 and LNCaP were harvested and washed once with PBS. After centrifugation, samples were incubated with 1:100 mouse isotype-PE (abcam) or mouse anti-PSMA-PE (abcam). After 30 min, samples were washed twice with PBS and run on FACScan. For each experiment, 10,000 events were gated. Samples were run in triplicate. All analysis was done using FlowJo software.

Mouse Handling

All animal handling and procedures were done in accordance with Institutional Animal Care and Use Committee protocols. For tumor studies, human xenograft prostate tumors were induced in six-to-eight week old male nude nu/nu mice (Charles River Laboratories). Mice were subcutaneously injected in the right flank with 3,000,000-4,000,000 LNCaP cells suspended with equal volume of Matrigel (BD Biosciences). Tumors were grown until they reached 3-7 mm in diameter. Mice were dosed with M13-SWNT probes by retro-orbital injection. For ex vivo analysis, mice were sacrificed at 24 h p.i. and organs were collected, measured and weighed.

Blood Circulation Study

Figure 7:
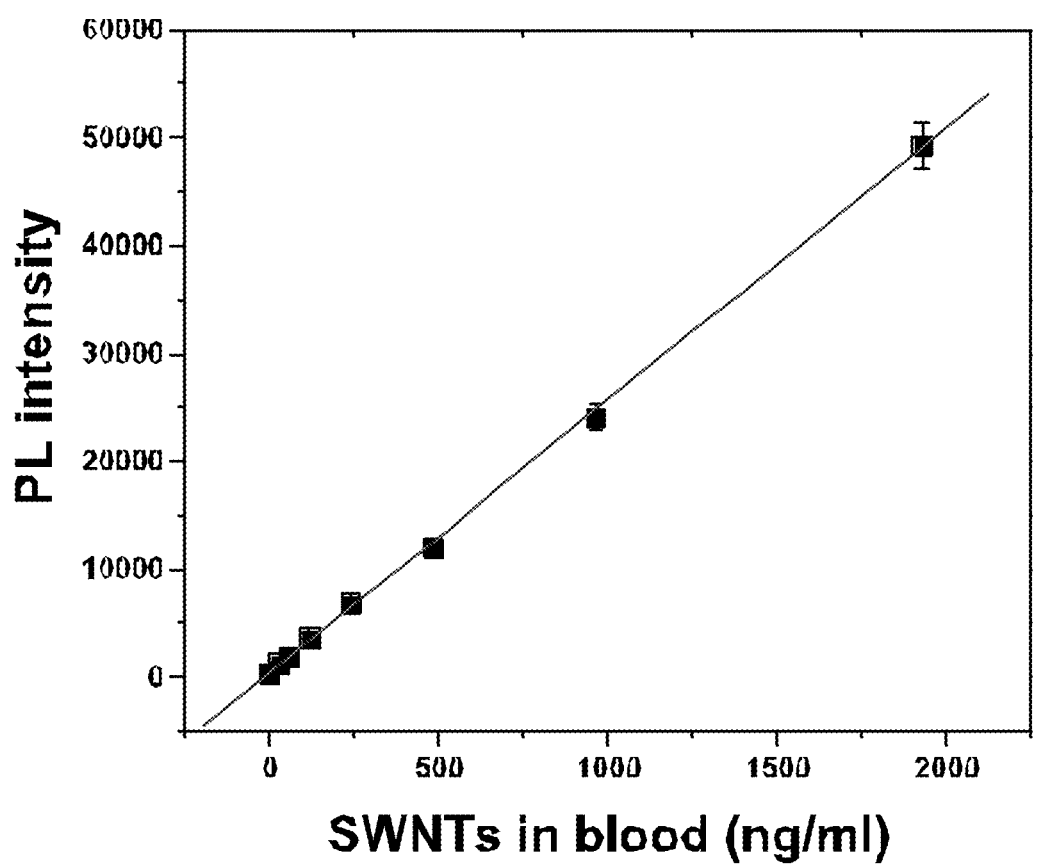
FIG. 7 illustrates calibration curve for the SWNT concentration in blood used for circulation study. The acquisition time was 0.5 s and the excitation fluence was ~120 mW/cm$^2$. The fitted line is PL intensity=392.8+25.266× [SWNTs] in ng/mL.
Figure 8:
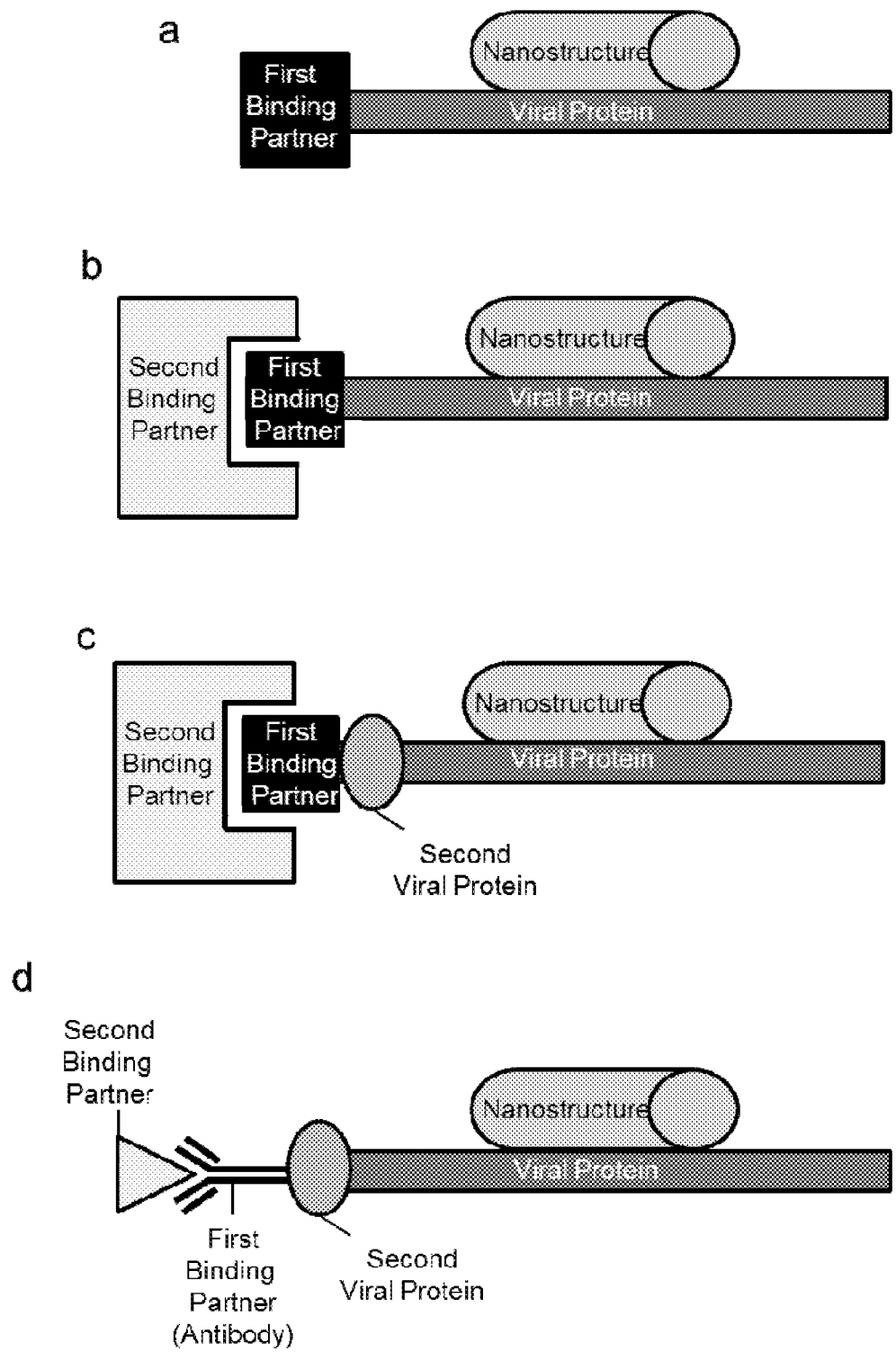
FIGS. 8a-8d are schematics of imaging probes.

For blood circulation, a few µl of blood was collected using a quartz capillary tube at each time point, and the NIR PL intensity of the blood samples was measured using the home-built imager (FIG. 2), described above. For quantitative analysis of the blood samples, a collimated laser was used. The actual fluence of the collimated laser on the sample was ~170 mW/cm$^2$ and the acquisition time was 0.5 s. To calculate % ID/g of SWNTs in blood, an equation, % ID/g={[SWNTs]$_{blood}$×V$_{blood}$×100}/{[SWNTs]$_{injected}$×V$_{injected}$=W$_{blood}$} was used. V$_{blood}$ and W$_{blood}$ were measured from each sample[S4]. The SWNTs concentration was calculated using a calibration curve (FIG. 7). For circulation study, three mice were used.

Near-Infrared Fluorescence Whole-Animal Imaging

Figure 2:
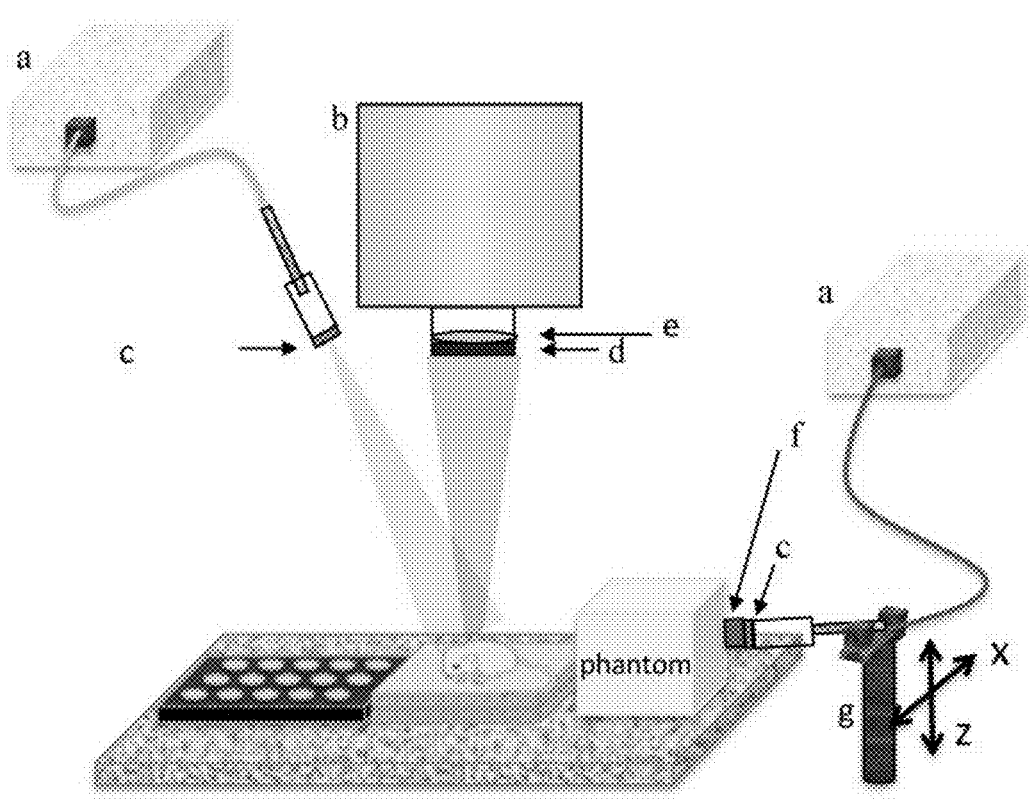
FIG. 2 is a schematic of a second near-infrared window fluorescence imager. The versatile imaging capability allows for in vivo imaging as well as in vitro screening and 3D stacked imaging of optical phantoms. a: 808 nm diode laser, b: liquid-nitrogen cooled two-dimensional InGaAs detector, c: 808 nm laser line filter, d: 1,100 nm long-pass filter, e: lens for NIR light, f: collimator, and g: stage controller for x- and z-directional travel of the laser.

An in vivo imager has been built for this study (FIG. 2). As a detector, a liquid nitrogen-cooled OMA V 2D InGaAs array detector (detection range: 800-1,700 nm) with a 256×320 pixel array (Princeton Instruments) was used. In front of the detector, NIR camera lens (SWIR-25, Navitar) was attached. To minimize autofluorescence from tissues and maximize the detection of fluorescence from SWNTs, two stacked long-pass filters with cut-off wavelength of 1,100 nm and OD>4 (EdmundOptics) were used. For the excitation, an optical fiber coupled 808 nm diode laser (MDL-F-808, OptoEngines) was used and a laser line filter with center wavelength of 808 nm (EdmundOptics) was attached in front of the laser to remove any unwanted excitation light. To minimize the exposure of the laser onto the mouse, a computer-controlled shutter was set-up. The actual fluence on the mouse for in vivo imaging was ~120 mW/cm$^2$. The acquisition time for in vivo imaging was 0.1 s~1 s. For the contrast images, the same detector was used but a white light was illuminated instead of an 808 nm laser.

Near-Infrared Fluorescence Imaging of M13-SWNTs in Phantoms

In the phantom study, to get depth information of the probe, a stacked 3D image was constructed. Phantoms were scanned along the depth direction with a scanning velocity of 0.5 mm/s, controlled by two-axis traveling stage controller (10 mm maximum travel length in each direction, Thorlabs), with a collimated laser of ~5 mm in diameter (collimator, F230SMA-B, Thorlabs), and fluorescence images of the phantom were collected every 0.5 s and were used to construct a 3D stacked image after background subtraction (Fiji, freeware).

In Vitro Binding Assay

To compare various binding ligands of M13-SWNTs, a binding assay was done using the imager. In a poly-lysine coated, black 96-well plate, 30,000 cells (either LNCaP or DU145) were plated in each well and 100 µL of complex solution with a concentration of 10$^{12}$/mL (SWNTs concentration: ~1 µg/mL) was added to each well, incubated at 37° C. for 4 h. After incubation, wells were washed three times with PBS and PL was measured. PL intensity was averaged over three wells. The acquisition time was 1 s for all samples.

Near-Infrared Fluorescence Microscopy

For NIR fluorescence imaging of sectioned tumor tissues, samples were excited by 658 nm laser and imaged and monitored using inverted microscope with liquid nitrogen-cooled OMA V 2D InGaAs detector and an AxioCam MRm charge-coupled device (CCD) camera.

Immunohistochemistry

Tissues and tumors were harvested, embedded in OCT resin and snap frozen in dry ice. Samples were cut into 5 μm sections. Immunostaining was done using ThermoScientific Autostainer 360. For immunostaining, sections were blocked with 3% $H_2O_2$ and blocked for endogenous mouse IgGs prior to incubation with 1:150 mouse anti-PSMA (Lifespan Biosciences) in PBS. Sections were then incubated with secondary horseradish peroxidase conjugate (ThermoScientific) and DAB chromogenic substrate (Ultravision). Samples were imaged using Olympus IX51 inverted microscope.

Imager Setup

For fluorescence imaging in the second optical window, an in-house in vivo imager was previously described[8]. A liquid nitrogen-cooled OMA V 2D InGaAs array detector (detection range: 800-1,700 nm) with a 256×320 pixel array (Princeton Instruments) was used. A NIR camera lens (SWIR-25, Navitar) was attached in front of the InGaAs detector. To reduce tissue autofluorescence and maximize the detection of fluorescence from SWNTs, two stacked long-pass filters with cut-off wavelength of 1,100 nm and OD>4 (EdmundOptics) were used. For excitation, an optical fiber coupled to an 808 nm diode laser (MDL-F-808, Opto-Engines) was used and a laser line filter with center wavelength of 808 nm (EdmundOptics) was attached in front of the laser to remove unwanted excitation light. To minimize laser exposure to animals, a computer-controlled shutter was incorporated into the imaging system. The measured fluence on the mouse for in vivo imaging was ~120 mW/cm². The acquisition time for in vivo imaging ranged from 0.01 s-1 s. For white contrast images, the same detector was used but the mice were illuminated with white light.

Blood and Ascites Stability and pH Measurements

For blood stability measurements, 20 ug/mL SBP-M13-SWNT was diluted in two-fold dilutions with PBS and then diluted 1:1 volume with blood obtained from healthy mice (Research Blood Components) and incubated for 0, 1, 2, 4, and 24 h. Samples were measured at the given time point using the NIR2 imager at 0.01 s exposure. For pH stability, SBP-M13-SWNT were calibrated to pH=4.5, 5.5. 6.5, 7.5, or 8.5 and samples were incubated 0, 1, 2, 4, and 24 h. Samples were measured using NIR2 imager at 0.01 s exposure and normalized to the baseline value.

Cell Viability Assay

To confirm OVCAR8 viability in the presence of SBP-M13-SWNT, 5,000 cells were seeded on 96 well plate and incubated with 10, 5, 2.5, 1.25, 0.62, and 0 ug/mL SBP-M13-SWNT. Twenty-four hours after probe incubation, alamar blue (Life Technologies) was added and fluorescence was measured 4 h post-addition, following manufacturer's recommendations. Viability was normalized to blank control. Samples were run in quadruplicate.

Cell Culture and Establishment of an Orthotopic Ovarian Cancer Model

All animal studies and procedures were approved by the MIT Institutional Animal Care and Use Committee. This study used the established human ovarian epithelial carcinoma cell line OVCAR8, engineered to constitutively express firefly luciferase. OVCAR8 cells were grown in RPMI 1640 medium containing 10% fetal bovine serum, penicillin, and streptomycin. Approximately 2×10⁶ OVCAR8 cells suspended in 200 μL DMEM (high glucose, phenol-red free) (Invitrogen) were implanted into the peritoneal cavity of athymic (nu/nu) mice to establish orthotopic ovarian cancer models. Mice were monitored by whole-animal bioluminescence imaging to assess tumor burden. Imaging experiments were performed approximately 7-14 days following tumor cell injection based on the measured bioluminescent intensity.

In Vivo Fluorescence Imaging of SBP-M13-SWNTs

SBP-M13-SWNTs were injected into the peritoneal cavity of tumor-bearing animals at ≈200 μg/kg. Mice were anesthetized with isoflurane gas. Fluorescence images were obtained approximately 24 hours following injection with exposure times ranging from 0.01 to 1 second for each subject. Background images were subtracted from raw images to generate the final images. Equivalent standardized regions of interest (ROIs) was constructed to determine tumor-to-background ratios at various locations within the peritoneal cavity. Comparisons of SBP-targeted and untargeted M13-SWNT probes were based on NIR fluorescent intensities of excised tumor nodules with normal intestinal tissue. Image intensities were quantified with ImageJ software.

Depth of Detection Limit of Tumors Labeled with SBP-M13-SWNT

Mice bearing OVCAR8 tumors were injected with ~200 ug/kg SBP-M13-SWNT. Twenty-four hours post-injection, tumors were excised. To determine the limit of detection by reflectance imaging, labeled tumors were cut into 1 mm diameter fragments and placed in a quartz capillary tube (Sutter Instruments). The quartz capillary tube was placed in a XFM-2 phantom mouse (Caliper) with the same optical properties of human tissue at 0, 4.3, 7.0, 9.7, or 18.2 mm depths. The fluorescence from the labeled tumor fragments was measured using the NIR2 imager at maximum aperture using 0.5 s exposure time. Background fluorescence images were also acquired before addition of labeled tumors. To quantify detection depth, background images were subtracted from acquired images of fluorescent tumors, and equivalent ROIs were drawn for images taken from each depth to calculated signal intensity.

SBP-M13-SWNT Imaging During Cytoreductive Surgery

Surgical studies were performed by a gynecologic surgeon. Animals were administered ≈200 μg/kg SBP-M13-SWNTs approximately 24 hours prior to surgery. For comparisons of initial cytoreduction with or without SWNT-guidance, animals were randomly assigned to one of these cohorts, and NIR2 fluorescence images were obtained 2-4 hours prior to surgery for all animals. For animals assigned to the SWNT-guided cohort, the whole-abdomen NIR2 fluorescence images were assessed by the surgeon prior to and during the surgical procedure. Excised nodules were measured, photographed, and imaged for SWNT-based fluorescence.

Immunohistochemistry and Fluorescence

Excised tissues were fixed in 10% formalin, embedded in paraffin, and sectioned for histology. Hematoxylin and eosin (H&E) staining was performed on tissue sections. For SPARC staining, rat anti-SPARC (1:40 dilution, R&D Systems) and rat isotype IgG (1:200, Abcam) were used with biotin-conjugated goat anti-rat antibody (Vector Labs, BA-9401), followed by the Vectastain ABC immunoperoxidase kit (Vector Labs, PA-6100) and DAB substrate (Vector Labs, SK-4100) for detection and visualization. For immunofluorescence, Alexa Fluor donkey anti-rat 488 secondary antibodies (Life Technologies) were used on frozen tissue sections. To visualize SBP-M13-SWNT by fluorescence, Alexa fluor 750 carboxylic acid, succinimidyl ester (Life Technologies) was conjugated to SBP-M13-SWNT via primary amine linkage following manufacturer's recommendations and excess dye was removed by extensive dialysis before usage.

EXAMPLES

Figure 4:
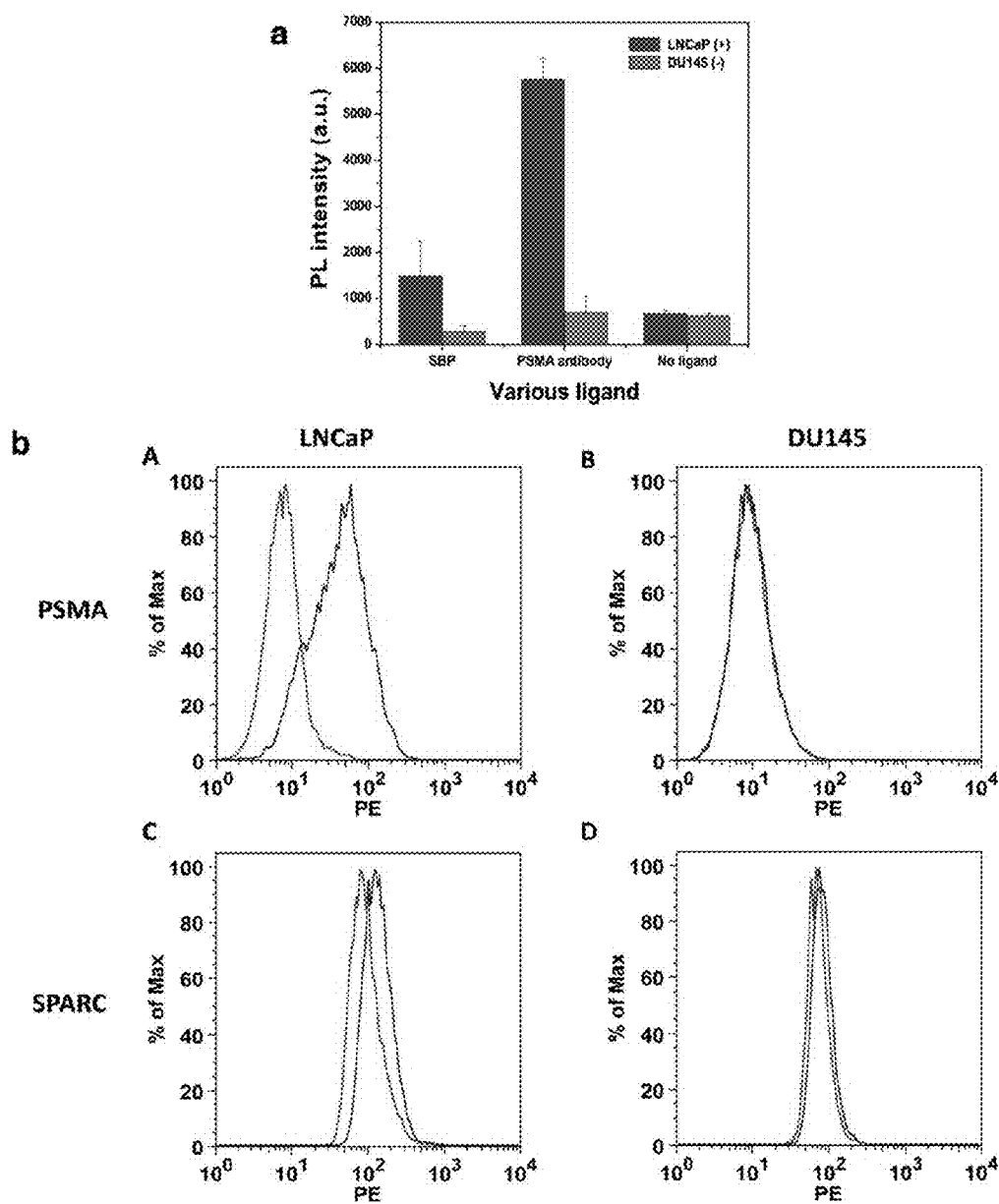
FIG. 4 illustrates targeting of the probe in vitro. a, In vitro binding assay of SBP, anti-PSMA, and no ligand displayed on the probe and incubated on LNCaP and DU145 prostate carcinoma cell lines. PL intensities are measured using custom-built imager. Acquisition times were 1 s for all samples. b, Expression of PSMA and SPARC in LNCaP and DU145 cell lines. FACS analysis shows expression of PSMA and SPARC in LNCaP (A, C blue histogram), respectively. Expression is not seen in DU145 cell line (B, D blue histogram). Red histogram is control.

To assess M13-SWNT as an efficient fluorescence imaging agent, optical properties and fluorescence stability of M13-SWNTs prepared as previously described were first investigated. Dang, X, 2011. In this study, SWNTs prepared by high-pressure carbon monoxide (HiPCO) were chosen rather than fluorescent semiconductor-rich CoMoCAT SWNTs since HiPCO SWNTs have more SWNT species with relatively large diameters which fluoresce at longer wavelengths (up to ~1,600 nm) than CoMoCAT SWNTs (up to ~1,100 nm). Dang, X, 2011. The absorption spectrum and PL excitation (PLE) map of the M13-SWNT probe in phosphate-buffered saline (PBS) was compared to SWNTs dispersed by 2 wt % sodium cholate (SC) in distilled water, denoted as SC-SWNTs (FIGS. 1b and 1c). The optical transition peaks of M13-SWNTs showed a small red shifting, most obvious in the lowest-energy interband transition (wavelengths >900 nm). The red shifting could be due to different dielectric environments surrounding the SWNTs after surfactant exchange with the M13 phage, and small bundling of SWNTs during the complexation. Choi, J. H.; Strano, M. S. Applied Physics Letters 2007, 90, (22), 223114, Dang, X, 2011, each of which incorporated by reference in its entirety. The relative quantum yield of M13-SWNT probe, calculated by comparing integrated PL intensity (957 nm-1,291 nm), was about 40% of the starting SC-SWNTs, and this relative quantum yield of M13-SWNTs was sufficient for in vivo imaging as shown later (FIG. 2a and FIG. 4a). To test fluorescence stability, the M13-SWNT probe in PBS was mixed with equal volume of either 100% fetal bovine serum (FBS) or cell culture media supplemented with 10% FBS, and NIR PL intensities of solutions were measured at various time points up to 24 h after mixing (FIG. 1d). M13-SWNTs in PBS and the culture media with 10% FBS retained their integrated PL intensity throughout the tested period, while the probe in FBS showed a slight decrease in the PL intensity after 3 h incubation. The decrease of PL intensity could be attributed to the adsorption of serum proteins on the sidewall of SWNTs because the surface of SWNTs bound by M13 is partially exposed to the solution. Cherukuri, P.; Gannon, C. J.; Leeuw, T. K.; Schmidt, H. K.; Smalley, R. E.; Curley, S. A.; Weisman, R. B. Proc Natl Acad Sci USA 2006, 103, (50), 18882-6, each of which is incorporated by reference in its entirety. However, the PL intensity remained around 90% after the initial decrease and did not show noticeable aggregation, indicating the probe was very stable. Kim, S.; Lim, Y. T.; Soltesz, E. G.; De Grand, A. M.; Lee, J.; Nakayama, A.; Parker, J. A.; Mihaljevic, T.; Laurence, R. G.; Dor, D. M.; Cohn, L. H.; Bawendi, M. G.; Frangioni, J. V. Nat Biotechnol 2004, 22, (1), 93-7, which is incorporated by refernece in its entirety. Therefore, these genetically engineered M13-stabilized fluorescence probes can be serum stable and brightly fluorescent, showing promise for in vivo imaging.

Figure 3:
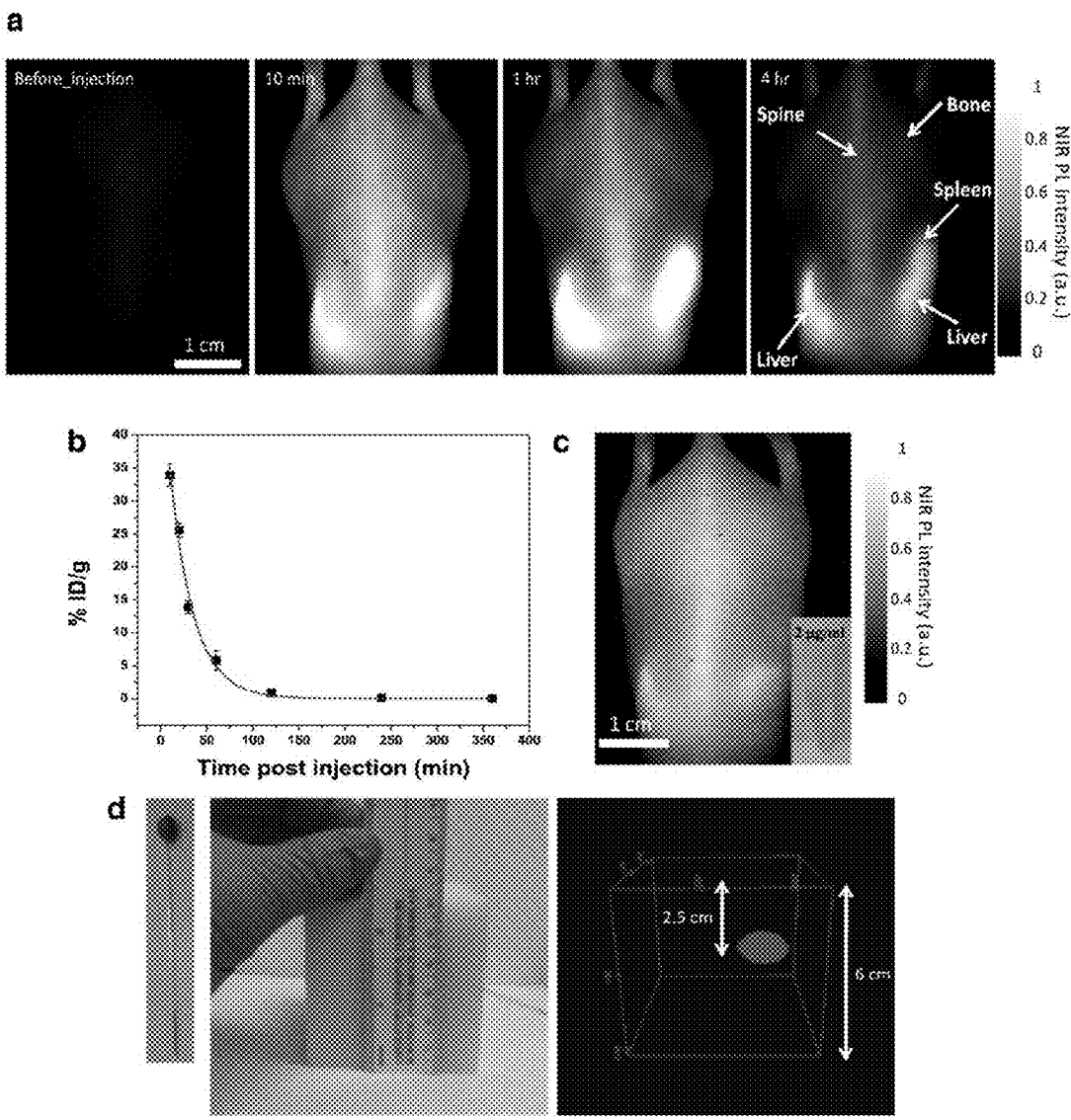
FIG. 3 illustrates the kinetics and sensitivity of the fluorescent M13-SWNT imaging probe. a, Fluorescence images of M13-SWNT injected mouse at various time points. At 10 min and 1 h post-injection (p.i.), vasculature and fenestrated kidneys can be observed. Dosage was 0.33 µg of SWNT/g (200 µL of 30 µg/mL SWNTs probe solution) and acquisition times for all images were 0.5 s. Signals from liver, spleen, bone, and spine are indicated by arrows. b, Blood circulation of M13-SWNT. The circulation time was determined as the timepoint when % ID/g of SWNT in blood falls to 5%, and the blood circulation of M13-SWNT was approximately 60 min. Each data point is the mean±s.d. from n=3 animals. c, Fluorescence image of a mouse injected with 2 µg/mL (200 µL, 0.022 mg/kg of SWNTs) probe solution. Liver and spleen are clearly seen on the dorsal side. Image was taken at 2 h p.i. Acquisition time was 0.5 s. d, Penetration depth of M13-SWNT in tissue-like phantom studies. Quartz capillary tube of M13-SWNT (left) is inserted into 6 cm³ tissue phantom (middle) and imaged using custom-built imager. Reconstructed 3D stacked image (right) shows M13-SWNT detectable at 2.5 cm depth.

The potential of the M13-SWNT probe for in vivo fluorescence imaging using a custom-built NIR imager (FIG. 2) was examined. Mice were imaged from the dorsal side before and after intravenous injection (FIG. 3a) with 200 μL of 30 μg/mL of SWNTs. Before injection, there was negligible tissue autofluorescence, which can be one of the advantages of second NIR window fluorescence imaging. At 10 min post-injection (p.i.), fluorescent M13-SWNTs were visualized throughout the vasculature and were evident in the highly fenestrated, vascular-rich kidneys. This vasculature was still visible but less obvious at 1 h p.i. and becomes featureless at 4 h p.i. . . . , consistent with the observed blood circulation behavior (FIG. 3b). The kinetics of M13-SWNT was beneficial for imaging since the ability to optimize tissue uptake while minimizing the background signal from circulation can be critical towards successful imaging. Weissleder, R. Science's STKE 2006, 312, (5777), 1168. Fluorescence from M13-SWNT probe was mostly observed in liver, spleen, and bone due to immune clearance by these organs of the reticuloendothelial system. Similar clearance has been reported with other nanomaterials including SWNTs and quantum dot (>20 nm) probes. Longmire, M.; Choyke, P. L.; Kobayashi, H. Nanomedicine (Lond) 2008, 3, (5), 703-17, Liu, Z.; Davis, C.; Cai, W.; He, L.; Chen, X.; Dai, H. Proc Natl Acad Sci USA 2008, 105, (5), 1410-5, Cai, W.; Shin, D. W.; Chen, K.; Gheysens, O.; Cao, Q.; Wang, S. X.; Gambhir, S. S.; Chen, X. Nano Lett 2006, 6, (4), 669-76, each of which is incorporated by reference in its entirety. It was noted that raw signal from liver and spleen was clearly detected from the dorsal side, which can be challenging to obtain using visible or first NIR window light. M13-SWNT probes in deep organs even at a low dosage of 2 μg/ml of SWNTs (0.022 mg/kg) (FIG. 3c) and up to 2.5 cm depth in tissue-like phantoms (FIG. 3d) could be detected. These low dosage and depth results highlight the advantages of the second NIR window fluorescent M13-SWNT probe.

Taking advantage of the versatility of the M13 scaffold, various targeting moieties were then incorporated into M13 and further screened for efficient targeting in vitro. To couple targeting functionality to SWNTs without compromising the fluorescence of SWNTs, minor coat protein p3, located at the proximal tip of M13 and spatially separated from SWNT-binding p8 proteins, was engineered to express either peptide ligands or peptide handles for site-specific antibody conjugation (FIG. 1a). A peptide identified from phage display against Secreted Protein, Acidic and Rich in Cysteine (SPARC) (SPARC-binding peptide, designated as SBP) was genetically engineered into the p3 protein of the SWNT binding M13. Kelly, K. A.; Waterman, P.; Weissleder, R. Neoplasia 2006, 8, (12), 1011-1018, which is incorporated by reference in its entirety. SPARC is a matricellular protein that can be overexpressed in various cancers, including prostate, breast and skin. Clark, C. J.; Sage, E. H. J Cell Biochem 2008, 104, (3), 721-32, which is incorporated by reference in its entirety. For an antibody binding system, a 15-amino acid biotin acceptor peptide (BAP) tag onto the p3 of M13 for site-specific conjugation of antibodies was engineered. Beckett, D.; Kovaleva, E.; Schatz, P. J. Protein Sci 1999, 8, (4), 921-9, which is incorporated by reference in entirety. The resulting BAP expressing M13 was biotinylated using birA biotin protein ligase enzyme in appropriate buffer conditions at 30° C. for 12 h. After the reaction, the biotinylated phage was purified by standard PEG/NaCl precipitation method. The enzymatically biotinylated peptide allowed the addition of any streptavidin-conjugated antibodies for desired targeting and removed the need for more complex and non-specific conjugation chemistries. An antibody against the extracellular domain of prostate specific membrane antigen (PSMA), a cell surface marker overexpressed in various prostate carcinomas and endothelium of tumor vasculature was conjugated. Wright, G. L., Jr.; Haley, C.; Beckett, M. L.; Schellhammer, P. F. Urol Oncol 1995, 1, (1), 18-28, Liu, H.; Moy, P.; Kim, S.; Xia, Y.; Rajasekaran, A.; Navarro, V.; Knudsen, B.; Bander, N. H. Cancer Res 1997, 57, (17), 3629-34, each of which is incorporated by reference in its entirety. To conjugate PSMA antibody to p3, approximately 500 µL of biotinylated phage-SWNT complex solution at $3 \times 10^{13}$ complexes/mL was incubated with 10 µL of streptavidin-conjugated antibody at room temperature for 12 h.

For screening, M13-SWNT probes displaying SPARC-binding peptide, PSMA antibody, or no ligand (denoted as SBP-M13-SWNT, anti-PSMA-M13-SWNT, and M13-SWNT, respectively) were incubated on LNCaP (higher SPARC expression and PSMA positive) and DU145 (low SPARC expression and PSMA negative) human prostate cancer cell lines and NIR fluorescence was measured to quantify specific uptake. There was about 5.3-fold and 8.3-fold enhanced uptake of SBP-M13-SWNT and anti-PSMA-M13-SWNT in LNCaP compared to DU145, respectively (FIG. 4a). In the control, there was only minimal background fluorescence present in DU145 and LNCaP and no targeting was observed. These results correlate with the expression level of PSMA and SPARC (FIG. 4b). Flow cytometry (Supporting Information) confirmed PSMA expression in LNCaP, whereas DU145 was negative for PSMA (FIG. 4b, top row). Moreover, there was moderate SPARC expression in LNCaP compared to DU145 control (FIG. 4b, bottom row). Interestingly, there was approximately 3.9-fold improvement in LNCaP targeting using anti-PSMA-M13-SWNT compared to SBP-M13-SWNT (FIG. 4a). This could be explained by the difference in the expression of cell surface markers, as confirmed by flow analysis. However, it was also possible that the different binding affinity of peptide versus antibodies may affect uptake. Ruoslahti, E.; Bhatia, S. N.; Sailor, M. J. Journal of Cell Biology 2010, 188, (6), 759-768, which is incorporated by reference in its entirety. By testing target and control cell lines, this in vitro assay allowed for screening of probes and to validate uptake and specificity of the probes.

Figure 5:
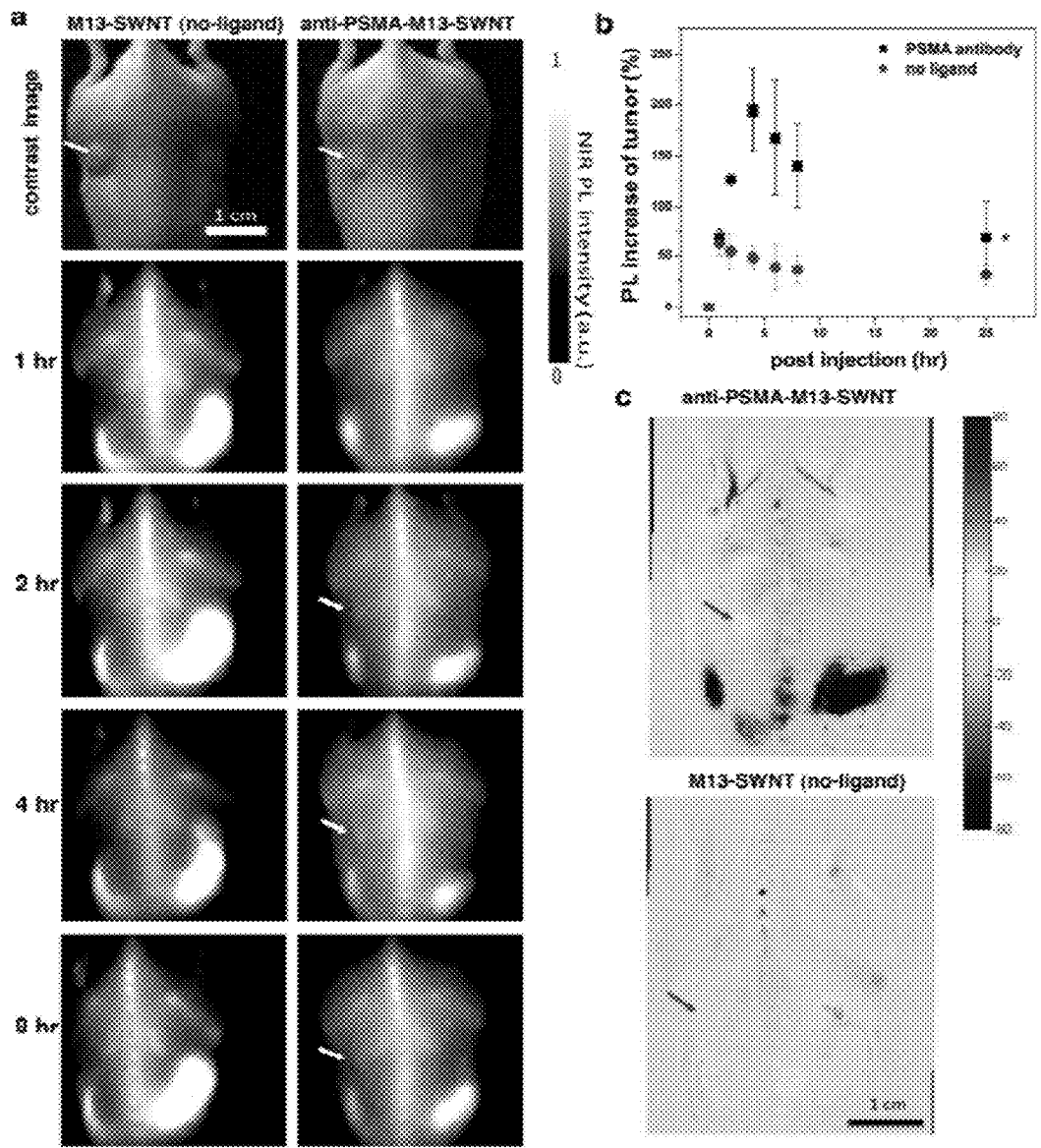
FIG. 5 illustrates in vivo targeting of tumors. a, In vivo second NIR window fluorescence images for LNCaP tumor-bearing mouse injected with anti-PSMA-M13-SWNT (right column) or control M13-SWNT (without ligand, left column) probes, taken at different time points. The clear tumor uptake of anti-PSMA-M13-SWNT injected mouse, maximized at 4 h p.i., shows active targeting capability of the probe. No obvious fluorescence image of tumors was observed throughout the timecourse when injected with control M13-SWNT (left column). Tumor areas are indicated by white arrows. All images are unprocessed, background-only subtracted. Acquisition times for the M13-SWNT mouse and the anti-PSMA-M13-SWNT mouse were 0.3 s and 0.5 s, respectively. b, Kinetics of tumor targeting. Each data point is the mean±s.d. from n=3 animals. *P <0.01 for the entire set of data compared to no-ligand, using student t-test for paired data with one-tailed distribution. c, Processed images of tumor accumulation of anti-PSMA-M13-SWNT (top) and control M13-SWNT (bottom) probes. Images collected at 1 h p.i. were subtracted from those at 4 h p.i.

Based on in vitro screening, anti-PSMA-M13-SWNT was identified as the best targeting candidate probe for subsequent investigation of tumor targeting and imaging in vivo. For the study of targeted imaging in vivo, human xenograft prostate tumors were induced in six-to-eight week old male nude nu/nu mice. Mice were subcutaneously injected in the right flank with $3 \times 10^6$-$4 \times 10^6$ LNCaP cells suspended with equal volume of Matrigel. Tumors were grown until they reached 3-7 mm in diameter. Upon formation of tumors, mice were injected intravenously with 200 µL of 30 µg/mL anti-PSMA-M13-SWNT and no targeting ligand control M13-SWNT and imaged at several intervals up to 24 h p.i. The fluorescence signal from anti-PSMA-M13-SWNT targeted tumor is clearly observed after 2 h and 4 h p.i. (FIG. 5a, indicated with white arrows) and reaches a maximum of ~200% increase in PL intensity at 4 h p.i. (FIG. 5a, right column and FIG. 5b). However, no obvious fluorescence image of tumor is observed when injected with control M13-SWNT probe (FIG. 5a, left column). Here, all the fluorescence images shown in FIG. 5a are unprocessed, background-only subtracted images. The tumor accumulation kinetics of anti-PSMA-M13-SWNT is compared to the control M13-SWNT by quantifying the regions of interest from the collected fluorescence images at different timepoints (FIG. 5b). At 4 h p.i., mice injected with anti-PSMA-M13-SWNT show four-fold improved relative tumor PL increase compared to control M13-SWNT, indicating targeted uptake. At this timepoint, the probe has already cleared circulation and has accumulated in tumors. Tumors injected with negative control M13-SWNT probe have an initial increase upon intravenous injection, but decrease and reach background levels, suggesting minimal accumulation (FIG. 5b). Interestingly, at 1 h p.i., both tumored mice show similar levels of PL increase (FIGS. 5a and 5b) due to circulating probes (FIG. 3b), making it difficult to specifically discern tumors at the earlier timepoints. The targeted accumulation of anti-PSMA-M13-SWNT compared to no ligand control M13-SWNT shown in FIG. 5a is further confirmed using image processing as presented in FIG. 5c. For image processing, fluorescence images collected at 1 h p.i. were subtracted from those at 4 h p.i. (FIG. 5a) after aligning the mouse positions using an image gradient based rigid registration to remove effects from translation and rotation of the mouse, followed with a deformable image registration to compensate for small deformations in limb positions and changes caused by breathing cycle, and the change of PL intensity is represented as scaled colors (FIG. 5c). Bergen, J. R.; Anandan, P.; Hanna, K. J.; Hingorani, R., Hierarchical Model-Based Motion Estimation. In Proceedings of the Second European Conference on Computer Vision, Springer-Verlag: 1992, Sand, P.; Teller, S. In Particle Video: Long-Range Motion Estimation using Point Trajectories, Computer Vision and Pattern Recognition, 2006 IEEE Computer Society Conference on, 2006, 2006; 2006; pp 2195-2202, each of which is incorporated by reference in its entirety. The positive number (red-side) indicates the increase of PL intensity and the negative value (blue-side) represents a decrease of PL intensity. The increase of PL intensity around tumor is clearly seen in the anti-PSMA-M13-SWNT-injected mouse whereas there is no obvious PL increase around tumor in the non-targeting probe-injected mouse, indicating the selective accumulation of probe in the targeting tumors. It is noted that in addition to the tumor, there are other areas showing PL intensity changes and these changes are mainly due to the misalignment while registering the two mouse positions.

After 4 h, there is a decrease of anti-PSMA-M13-SWNT accumulation in tumors (FIGS. 5a, right and 5b), and this behavior may be mediated by M13 phage. Probes targeting molecules overexpressed in tumor vasculature can exit, leading to decreased tumor accumulation at later time points. Since M13 is a large macromolecule (>200 nm) and less likely to penetrate the vascular wall compared to small drugs or peptides, it likely targets PSMA also overexpressed in the tumor vasculature. Liu (1997); Ruoslahti (2010). It is feasible that the decrease of PL intensity observed in both non-targeted and targeted probes may be partially due to the possible degradation of M13 phage by metabolic activity of cells and tissues, leading to bundling of SWNTs and quenching of their fluorescence. However, this behavior would occur with both non-targeted and targeted probes and therefore the PL difference between probes can still be attributed to targeted uptake.

Figure 6:
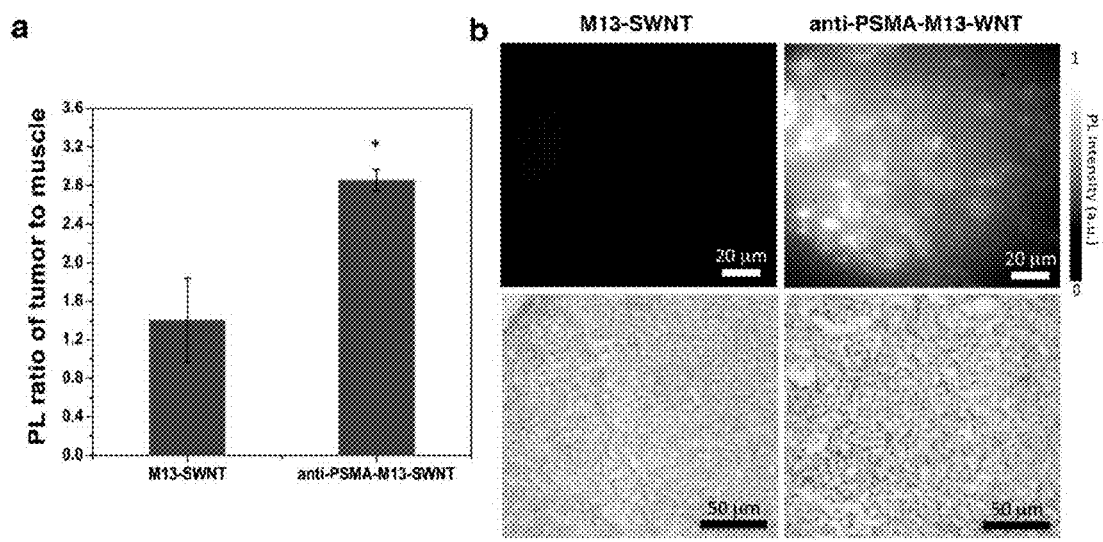
FIG. 6 illustrates ex vivo analysis of tumor targeting. a, Relative targeted tumor uptake of anti-PSMA-M13-SWNT compared to no ligand control was determined from NIR PL intensity ratios of tumor to muscle. Tumors and muscles were collected at 24 h p.i. Acquisition times for all samples were 0.5 s. Each data point is the mean±s.d. from n=3 animals. *P<0.05 compared to no-ligand, using student t-test for paired data with one-tailed distribution. b, Probe uptake in vivo and immunohistochemistry (IHC) (lower row). LNCaP tumors were injected with anti-PSMA-M13-SWNT or M13-SWNT (without ligand) probe, shown in the right column and left column respectively. Five micron-cut serial sections were measured for SWNT fluorescence (upper row) and stained for PSMA expression (brown) (bottom row). PSMA expression in both tumors confirms anti-PSMA-M13-SWNT uptake (upper right panel) is specific and non-artifactual. The acquisition times for PL microscopy were 1 s and images for IHC were taken at 15 ms.

To further confirm targeting, probe uptake in tumors was analyzed ex vivo. To quantify tumor uptake relative to muscle background, fluorescent images of the tumor and muscle excised at 24 hr p.i. were acquired and fluorescent intensities of image regions of interest were obtained. The NIR PL ratio of tumor to muscle of anti-PSMA-M13-SWNT is ~2.9 and this ratio is about two fold higher than non-targeted M13-SWNT (~1.4) (FIG. 6a), indicating preferential tumor uptake of anti-PSMA-M13-SWNT. Anti-PSMA-M13-SWNT uptake at the microscale was confirmed by NIR fluorescent microscopy. Harvested tissues and tumors were embedded in OCT resin and snap frozen in dry ice, and then cut into five micron sections. NIR fluorescence microscopy of sectioned tumors confirms anti-PSMA-M13-SWNT accumulation (FIG. 6b, upper right panel), whereas M13-SWNT is not seen in tumors (FIG. 6b, upper left panel). To validate uptake is specific and selective, PSMA expression on both tumors were examined through immunostaining. Adjacent tumor sections were probed with anti-PSMA antibody and secondary horseradish peroxidase conjugate and incubated with DAB chromogenic substrate. The resulting brown color of tumor sections (FIG. 6b, bottom row) is indicative of PSMA expression in both tumors, confirming uptake of anti-PSMA-M13-SWNT is specific and not artifactual.

It is noted that the two-fold improvement in PSMA targeting in vivo achieved in this work is equivalent to results reported by others targeting PSMA using aptamers and antibodies with diblock polymers, quantum dots, and indocyanine green conjugates. Gu, F.; Zhang, L.; Teply, B. A.; Mann, N.; Wang, A.; Radovic-Moreno, A. F.; Langer, R.; Farokhzad, O. C. Proc Natl Acad Sci USA 2008, 105, (7), 2586-91, Shi, C.; Zhu, Y.; Xie, Z.; Qian, W.; Hsieh, C. L.; Nie, S.; Su, Y.; Zhau, H. E.; Chung, L. W. Urology 2009, 74, (2), 446-51, Nakajima, T.; Mitsunaga, M.; Bander, N. H.; Heston, W. D.; Choyke, P. L.; Kobayashi, H. Bioconjug Chem 2011, 22, (8), 1700-5, each of which is incorporated by reference in its entirety. Increasing targeting efficiency of nanoparticles is a challenge to the nanomedicine community. To improve targeting of the phage-based nanoprobes, other combinations of targeting ligands/antibodies and receptors could be exploited. Moreover, the phage targeting platform can be combined with methods to further amplify tumor targeting, including bioorthogonal chemistries for pre-targeting, biomimetic amplification, and communicating nanoparticles. Devaraj, N. K.; Weissleder, R.; Hilderbrand, S. A. Bioconjug Chem 2008, 19, (12), 2297-9, Simberg, D.; Duza, T.; Park, J. H.; Essler, M.; Pilch, J.; Zhang, L.; Derfus, A. M.; Yang, M.; Hoffman, R. M.; Bhatia, S.; Sailor, M. J.; Ruoslahti, E. Proc Natl Acad Sci USA 2007, 104, (3), 932-6, von Maltzahn, G.; Park, J. H.; Lin, K. Y.; Singh, N.; Schwoppe, C.; Mesters, R.; Berdel, W. E.; Ruoslahti, E.; Sailor, M. J.; Bhatia, S. N. Nat Mater 2011, 10, (7), 545-52, each of which is incorporated by reference in its entirety.

In addition to enabling targeted fluorescence imaging of tumors in the longer wavelength window (beyond 1000 nm), the phage-based probe could offer other unique opportunities. First, due to the filamentous structure and genetically modifiable various capsid proteins of M13, multiple imaging nanoparticles or SWNTs can be loaded along the phage and targeting ligands can be conjugated onto the tip of the phage site-specifically, enabling delivery of a higher payload of nanoparticles to receptors, thereby enhancing detection sensitivity. This configuration is difficult to achieve with other nanoparticle-based imaging schemes and this scheme will be particularly useful when the target receptor density of the tumor cells is low. Second, since there are more functional groups for further modification on major coat protein, p8, and the other tip protein, p9, of the phage, different nanoparticles such as gold nanorods or iron oxides can be easily conjugated onto the phage for enhanced fluorescence or multimodality imaging.

Using genetically modified multifunctional M13 phage as a template to assemble fluorescent single-walled carbon nanotubes (SWNTs) and ligands, SWNTs have now be successfully utilized for second NIR window fluorescence imaging of molecularly targeted tumors for the first time. By engineering multiple capsid proteins of M13 phage independently, targeting capability is incorporated into SWNTs without compromising the in vivo stability of the fluorescence of SWNTs. M13-SWNT probe was detectable in deep tissues even at a low dosage (2 µg/mL) and up to 2.5 cm in tissue-like phantoms, showing the potential for early, non-invasive diagnosis and clinical procedures, such as intraoperative surgery. Whitney, M. A.; Crisp, J. L.; Nguyen, L. T.; Friedman, B.; Gross, L. A.; Steinbach, P.; Tsien, R. Y.; Nguyen, Q. T. Nat Biotechnol 2011, 29, (4), 352-6, Nguyen, Q. T.; Olson, E. S.; Aguilera, T. A.; Jiang, T.; Scadeng, M.; Ellies, L. G.; Tsien, R. Y. Proceedings of the National Academy of Sciences of the United States of America 2010, 107, (9), 4317-4322, each of which is incorporated by reference in its entirety.

Future work to develop image processing methods and enhance signal amplification of M13-SWNT through utilizing longer SWNTs, additional genetic engineering of the M13 phage for multiple peptide display, and synthesizing hybrid materials for metal enhanced fluorescence of SWNTs, and further amplify tumor targeting utilizing bioorthogonal chemistries for pre-targeting, biomimetic amplification, and communicating nanoparticles will allow us to image traditionally hard-to-detect areas. Gu, F.; Zhang, L.; Teply, B. A.; Mann, N.; Wang, A.; Radovic-Moreno, A. F.; Langer, R.; Farokhzad, P. C. Proc Natl Acad Sci USA 2008, 105, (7), 2586-91, Shi, C.; Zhu, Y.; Xie, Z.; Qian, W.; Hsieh, C. L.; Nie, S.; Su, Y.; Zhau, H. E.; Chung, L. W. Urology 2009, 74, (2), 446-51, Nakajima, T.; Mitsunaga, M.; Bander, N. H.; Heston, W. D.; Choyke, P. L.; Kobayashi, H. Bioconjug Chem 2011, 22, (8), 1700-5, Devaraj, N. K.; Weissleder, R.; Hilderbrand, S. A. Bioconjug Chem 2008, 19, (12), 2297-9, Simberg, D.; Duza, T.; Park, J. H.; Essler, M.; Pilch, J.; Zhang, L.; Derfus, A. M.; Yang, M.; Hoffman, R. M.; Bhatia, S.; Sailor, M. J.; Ruoslahti, E. Proc Natl Acad Sci USA 2007, 104, (3), 932-6, von Maltzahn, G.; Park, J. H.; Lin, K. Y.; Singh, N.; Schwoppe, C.; Mesters, R.; Berdel, W. E.; Ruoslahti, E.; Sailor, M. J.; Bhatia, S. N. Nat Mater 2011, 10, (7), 545-52, Hong, G.; Tabakman, S. M.; Welsher, K.; Chen, Z.; Robinson, J. T.; Wang, H.; Zhang, B.; Dai, H. Angew Chem hit Ed Engl 2011, 50, (20), 4644-8, Choi, J. H.; Nguyen, F. T.; Barone, P. W.; Heller, D. A.; Moll, A. E.; Patel, D.; Boppart, S. A.; Strano, M. S. Nano Lett 2007, 7, (4), 861-7, Whitney, M. A.; Crisp, J. L.; Nguyen, L. T.; Friedman, B.; Gross, L. A.; Steinbach, P.; Tsien, R. Y.; Nguyen, Q. T. Nat Biotechnol 2011, 29, (4), 352-6, Nguyen, Q. T.; Olson, E. S.; Aguilera, T. A.; Jiang, T.; Scadeng, M.; Ellies, L. G.; Tsien, R. Y. Proceedings of the National Academy of Sciences of the United States of America 2010, 107, (9), 4317-4322, Welsher, K.; Sherlock, S. P.; Dai, H. Proc Natl Acad Sci USA 2011, Rajan, A.; Strano, M. S.; Heller, D. A.; Hertel, T.; Schulten, K. J Phys Chem B 2008, 112, (19), 6211-3, Nam, K. T.; Kim, D. W.; Yoo, P. J.; Chiang, C. Y.; Meethong, N.; Hammond, P. T.; Chiang, Y. M.; Belcher, A. M. Science 2006, 312, (5775), 885-8. each of which is incorporated by reference in its entirety.

A number of embodiments of the invention have been described. Nevertheless, it will be understood that various modifications may be made without departing from the spirit and scope of the invention. Accordingly, other embodiments are within the scope of the following claims.

Use of M13-SWNT for Sensing *E. Coli*

In one embodiment, M13-SWNT complex can be used directly to detect, locate, image and monitor pathogenic infection of *Escherichia coli* (*E. coli*). M13 bacteriophage can attach and bind to only strains of *E. coli* which express the F-pili appendages on their surface. In one example of this application, *E. coli* of two different strains, DH5-α (New England Biolabs, MA, USA) and JM109 (Promega, Wis., USA) were used, of which the former lacks F-pili, the latter is F-pilus positive.

Figure 10:
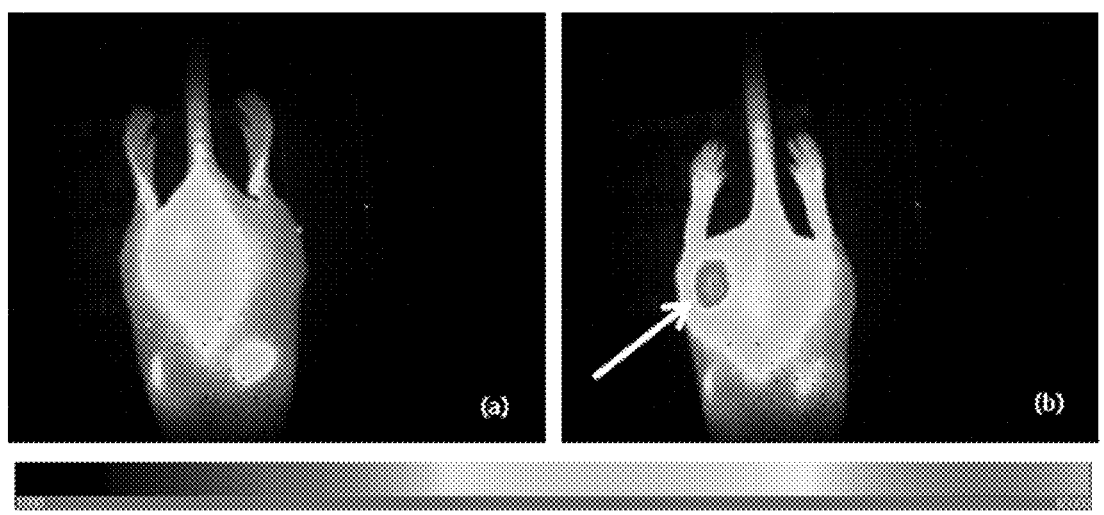
FIG. 10 illustrates NIR-II fluorescence image of a mouse injected with M13-SWNT probe, having an (a) DH5-α infection of *E. coli* (first group) or (b) JM-109 infection (second group). A factor of 2× increase in fluorescence intensity is observed from the JM109 strain, which has the F-pilus necessary for attachment of the M13 bacteriophage, compared to the DH5-α strain which lacks this F-pilus. The scale bar is from 1000 to 65000 (intensity counts). Both images have been normalized to the same range of intensities. Representative t=24 hr.

Two groups of N=5 mice each were studied, with one group receiving the DH5-α strain and the second group receiving the JM109. The mice used for this study were female nude nu/nu mice, 43-56 days old (strain 088, Charles River Laboratories, MA, USA). $10^8$ cells of bacteria in 50 µL LB media were injected in the right caudal thigh muscle using a 25 gauge needle. As a control, 50 µL of 1×PBS was also injected in the left thigh. After incubating the bacteria in the living host for 1 hr., the M13-SWNT probe was injected into the circulation through a retro-orbital injection. The time of injection of the M13-SWNT probe was taken as t=0. Post injection, mice were imaged at t=1, 2, 4, 8, and 24 hr. A custom-built fluorescence whole-animal imaging instrument described previously was used for this purpose. Yi H. et al, Nano Lett. 2012, 12, 1176-1183, which is incorporated by reference in its entirety. This instrument uses an excitation laser at a wavelength of 808 nm, and two long-pass emission filters at 1100 nm. The camera comprises of a liquid-nitrogen cooled 2D InGaAs sensor (Princeton Instruments, NJ, USA) with a full-frame 320×256 pixel array. The peak fluorescence signal intensity is observed at t=24 hr (data shown here). FIG. 10 compares the ability of the M13-SWNT probe to distinguish between F-negative DH5-α and the F-positive JM109 strains. A 2-fold increase in fluorescence intensity (white arrow, FIG. 10b) at the site of the JM109 infection was observed, corresponding to an enhanced localization of the M13-SWNT probe, compared to the DH5-α infection.

Use of M13-SWNT for Sensing Other Bacteria

To enable the M13-SWNT complex to selectively conjugate to other strains of bacteria which do not natively have F-pili, a 1-step tuning process can be used. Previously, a method has been reported to express biotin acceptor peptide (BAP), GLNDIFEAQKIEWHE, on the p3 coat protein of the M13 bacteriophage. Yi H. et al, Nano Lett. 2012, 12, 1176-1183; Beckett D. et al, Protein Sci 1999, 8, 921-929, each of which is incorporated by reference in its entirety. M13-SWNTs expressing BAP (BAP-M13-SWNT) is then enzymatically biotinylated at the lysine residue (Lys10) using a biotin-protein ligase (Avidity, Colo., USA). The biotinylated peptide acts as a handle and allows for site-specific conjugation of streptavidin-conjugated antibodies for desired targeting. In the present invention, antibodies against bacteria are complexed to streptavidin using a commercially available kit (EasyLink Streptavidin kit, abcam, Cambridge, Mass.). This complex is then reacted with biotinylated BAP-M13-SWNT to develop probes (anti-bacterial antibody-M13-SWNT) for targeting against specific bacterial infections.

In one embodiment, this probe was used to conjugate anti-*Staphylococcus aureus* antibody (anti-*S. aureus*-M13-SWNT). Mouse IgG3 *Staphylococcus aureus* monoclonal antibody (Pierce Biotechnology, Ill., USA) was used. This probe can be used to detect, locate, image and monitor *S. aureus* infection. In one example of this application, Xen-29 (Caliper Life Sciences, MA, USA) strain of *S. aureus* was used for inducing infection. $10^8$ cells of bacteria in 50 µL LB media were injected in the right caudal thigh muscle using a 25 gauge needle. As a control, 50 µL of 1×PBS was also injected in the left thigh.

Figure 11:
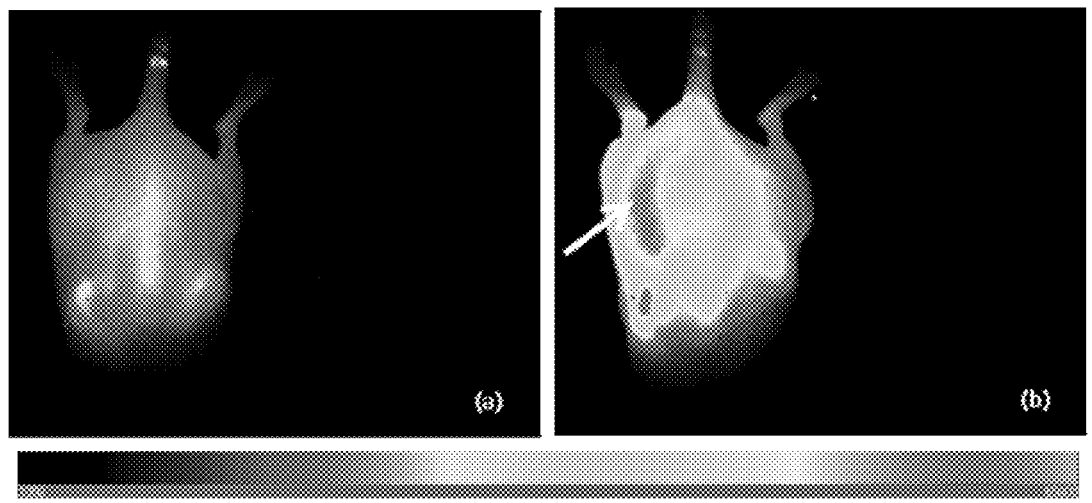
FIG. 11 illustrates near-infrared fluorescence image of a mouse injected with (a) M13-SWNT probe, and (b) anti-*S. aureus*-M13-SWNT probe. A factor of 3× increase in intensity is observed for the probe with the anti-*S. aureus* antibody, compared to the non-targeted M13-SWNT probe. The scale bar is from 1000 to 65000 (intensity counts). Both images have been normalized to the same range of intensities. Representative t=8 hr.

Two groups of N=5 mice each were studied, with one group receiving only M13-SWNT probe (negative control), and the second group receiving the anti-*S. aureus*-M13-SWNT. After incubating the bacteria in the living host for 1 hr., the M13-SWNT (or anti-*S. aureus*-M13-SWNT, depending upon the group) probe was injected into the circulation through a retro-orbital injection. The time of injection of the probe was taken as t=0. Post injection, mice were imaged at t=1, 2, 4, 8, and 24 hr. using the same imaging instrument described above. The peak fluorescence signal intensity is observed at t=8 hr (data shown here). FIG. 11 compares the ability of the targeted anti-*S. aureus*-M13-SWNT probe to detect and locate *S. aureus* infections in living hosts, compared to non-targeted M13-SWNT. A 3-fold increase in fluorescence intensity was observed (white arrow, FIG. 11b), corresponding to an enhanced localization of the anti-*S. aureus*-M13-SWNT probe aided by antibody targeting.

Use of M13-SWNT for Surgical Guidance

Figure 12:
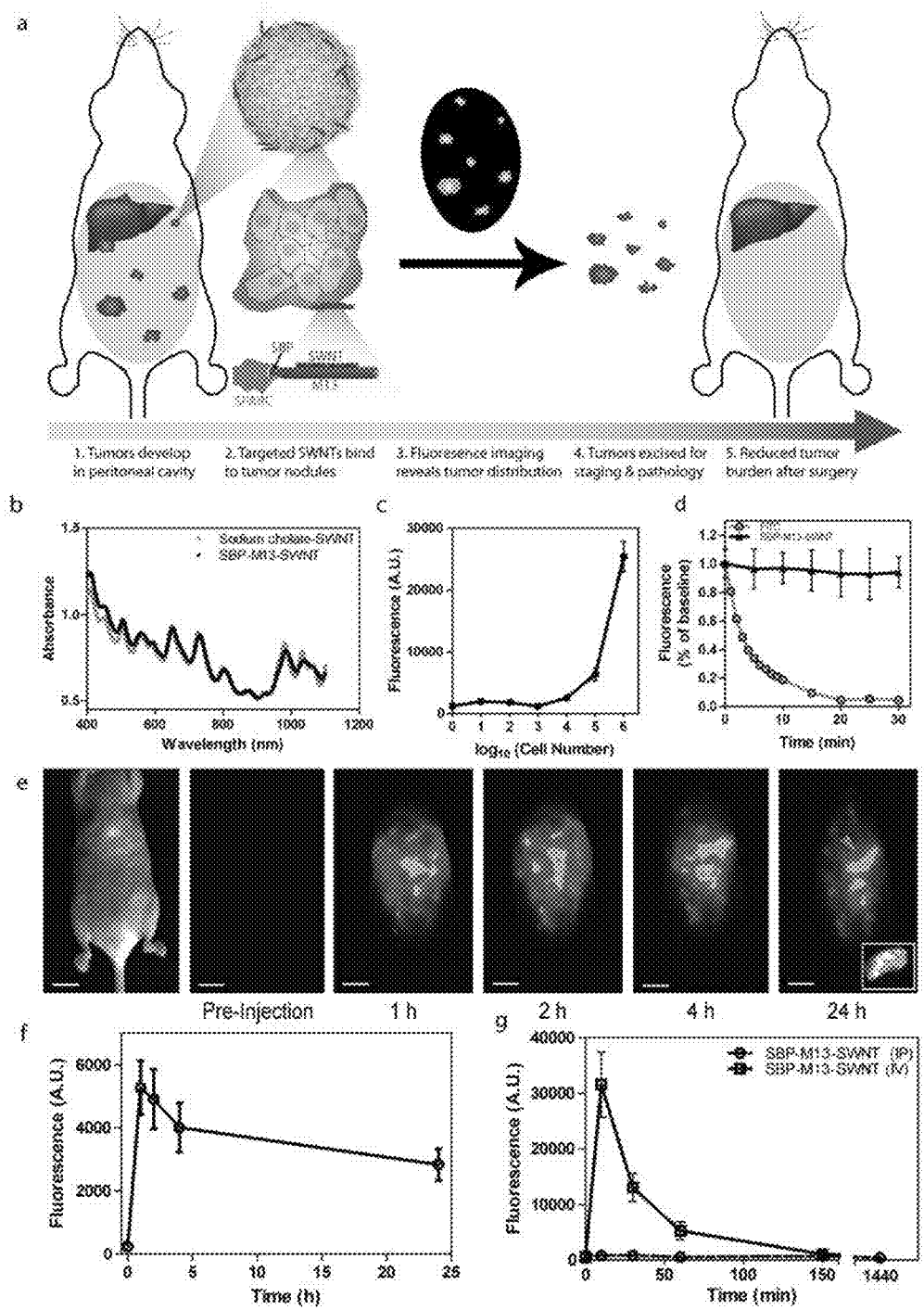
FIG. 12 illustrates characterization of Tumor-Targeting SBP-M13-SWNT Probe. a, Schematic illustrating association with ovarian tumor nodules for non-invasive detection by NIR2 fluorescence and surgical excision. b, Absorbance spectra of SWNTs in sodium cholate and as SBP-M13-SWNT probe. c, In vitro sensitivity of SBP-M13-SWNT fluorescence in ovarian cancer cell culture. d, Photobleaching fluorescence decay of FITC and SBP-M13-SWNTs under continuous excitation. e, Representative whole abdomen NIR2 imaging series following intraperitoneal administration of SBP-M13-SWNTs. Inset (far right): Surgically excised OVCAR8 tumor nodule (denoted by red arrow) observed 24 hours post-injection of M13-SBP-SWNTs. F, NIR2 fluorescence intensity in the abdomen of tumor-bearing animals following IP administration of M13-SBP-SWNTs up to 24 hours post-injection. (n=5) g, Pharmacokinetic circulation study of SBP-M13-SWNT administered intravenously (IV) and intraperitoneally (IP). Scale bars: 1 cm (e)

The imaging probe (SBP-M13-SWNT) consists of three fundamental components: the SPARC binding peptide (SBP), M13 virus (M13), and single-walled carbon nanotubes (SWNTs). The filamentous M13 virus (6 nm diameter, 880 nm length) disperses and stabilizes the SWNTs to permit targeted imaging (FIG. 12a). M13 is easily genetically modifiable to incorporate peptides for display on the various coat proteins of the virus; the modularity of M13 can be exploited to target various biomarkers in cancers, highlighting its attractiveness as a multifunctional probe. Phage display can be used to identify a peptide along the p8 major coat protein of M13 that binds and stabilizes SWNTs, while retaining the optical and electronic properties of the nanotubes. Dang X. et al., Nat Nanotechnol 2011, 6, 377-384, which is incorporated by reference in its entirety. Because M13 is amenable to genetic modification for peptide display, the p3 minor coat protein was further engineered to display a targeting peptide that binds SPARC (for Secreted Protein, Acidic and Rich in Cysteine). SPARC is a matricellular protein highly expressed in certain subtypes of breast, prostate, and ovarian cancer. SPARC overexpression has been shown to enhance ovarian cancer cell proliferation, invasion and metastasis. High levels of SPARC expression have been associated with high stage of ovarian carcinoma and correlated with poor clinical prognosis, suggesting its relevance as a clinical biomarker. Chen J. et al., PLoS One 2012, 7, e42413, which is incorporated by reference in its entirety. Collectively, this engineered imaging probe will enable us to localize, detect, and surgically excise ovarian tumors, as outlined in the schematic presented in FIG. 12a.

Before targeting tumors in vivo, the optical properties of SBP-M13-SWNTs were examined. Compared to unmodified SWNTs dispersed in sodium cholate, complexed SBP-M13-SWNTs exhibit similar optical absorbance (FIG. 12b). Photoluminescence (fluorescence) mapping of the excitation and emission wavelengths of SBP-M13-SWNTs suggests M13-stabilized SWNTs retain their fluorescent properties (Supplementary Information); non-dispersed, aggregating or bundled SWNTs would quench and not fluoresce, and thus, not appear in the fluorescence mapping.

Figure 15:
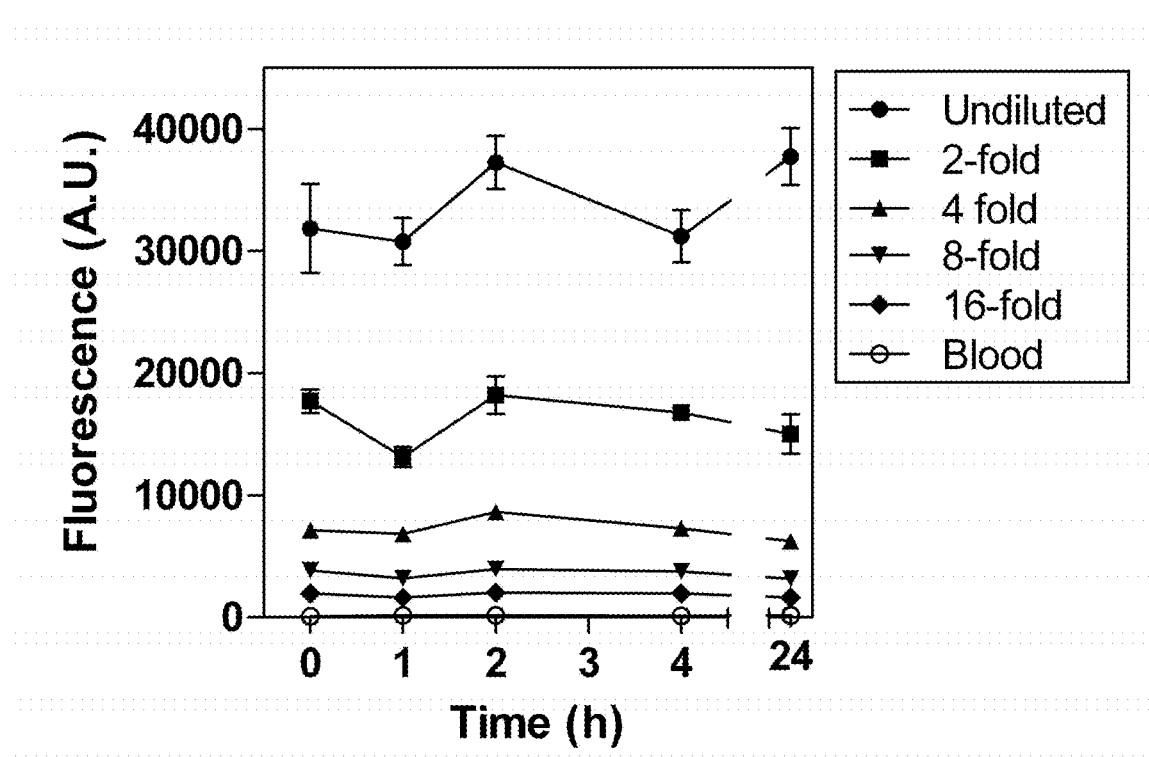
FIG. 15 illustrates stability of SBP-M13-SWNTs in blood. Serial two-fold dilutions of SBP-M13-SWNTs were incubated in blood to assess detection range and stability of the imaging probe in an in vivo environment for periods up to 24 hours. NIR2 fluorescence measurements directly correlated with concentration of SBP-M13-SWNT, and the fluorescence remained stable for periods up to 24 hours. Dilutions were measured in duplicate. Error bars denote standard deviation.
Figure 16:
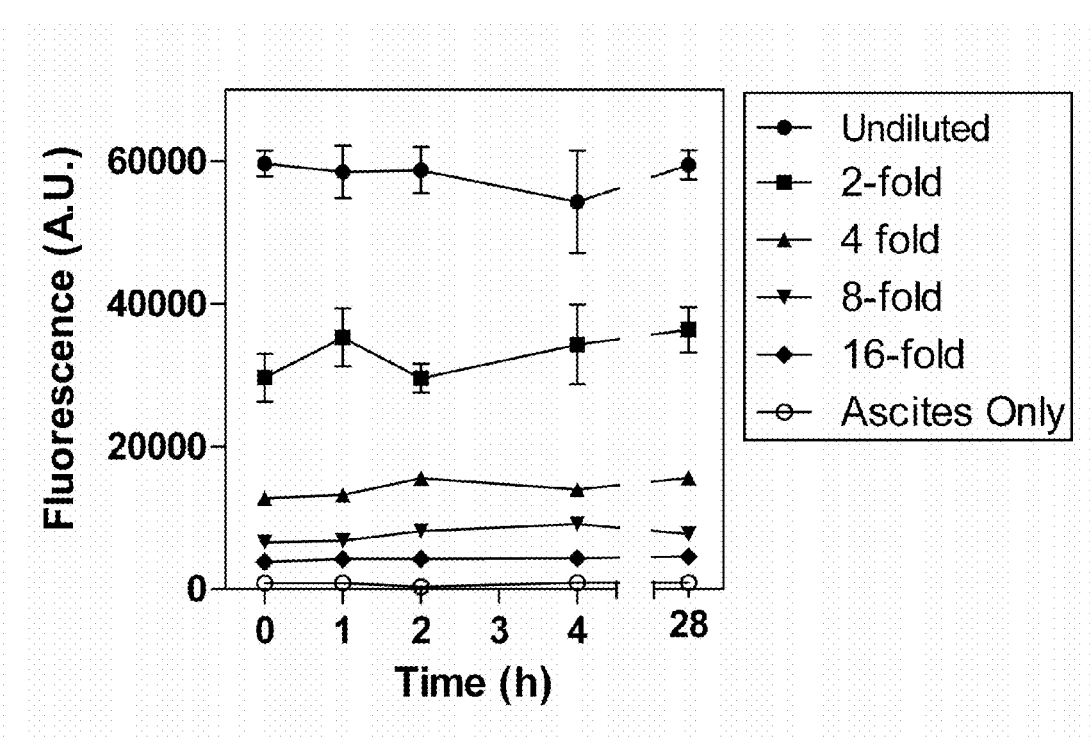
FIG. 16 illustrates stability of SBP-M13-SWNTs in ascites. Serial two-fold dilutions of SBP-M13-SWNTs were incubated in ascites harvested from a tumor-bearing mouse to assess stability and detection limit of the imaging probe for periods up to 28 hours. Fluorescent signal was directly proportional to concentration of SBP-M13-SWNT in ascites. Dilutions were measured in duplicate. Error bars denote standard deviation.
Figure 17:
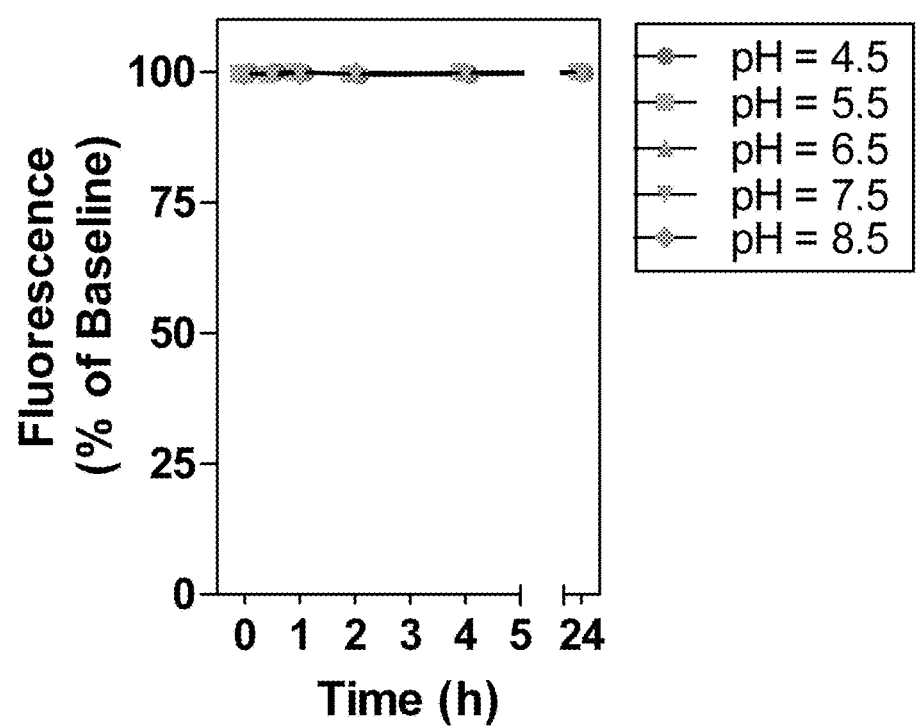
FIG. 17 illustrates pH stability of SBP-M13-SWNTs. SBP-M13-SWNTs were incubated at pHs between 4.5-8.5 for periods up to 24 hours. NIR2 fluorescence measurements were unaffected by pH of the solution for periods up to 24 hours. Samples were measured in duplicate. Error bars denote standard error.
Figure 18:
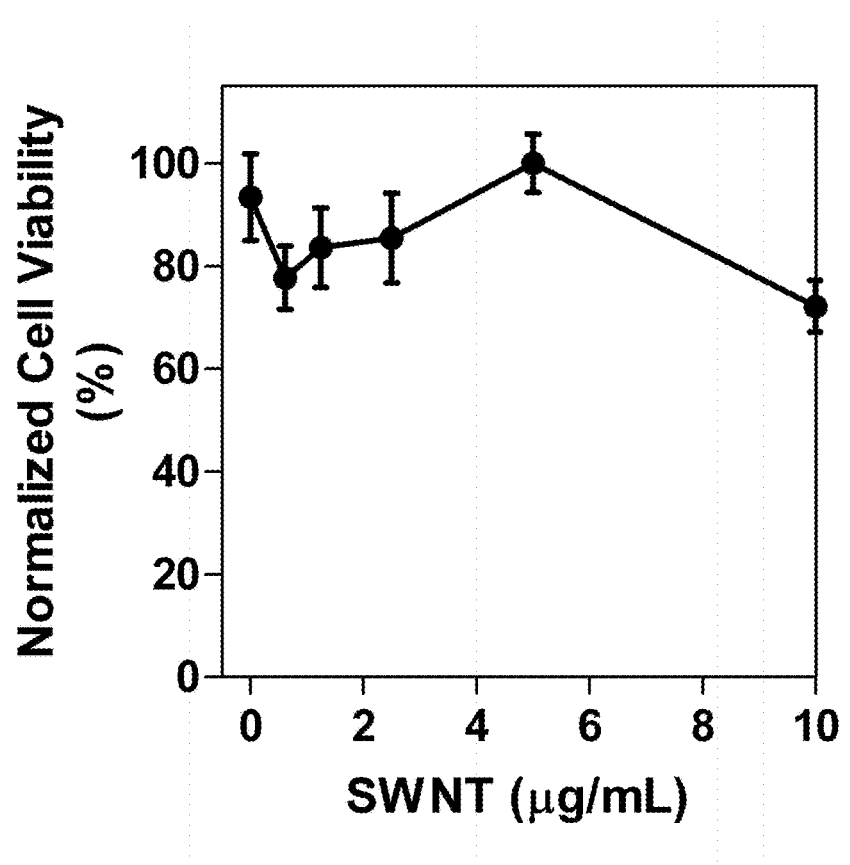
FIG. 18 illustrates OVCAR-8 viability in presence of SBP-M13-SWNTs. Cells incubated in the presence of SBP-M13-SWNTs remain viable at [SBP-M13-SWNT] between 0-10 ug/mL. Six samples were run for each experimental condition. Error bars denote standard error (n=6).

To establish their use for in vivo applications, the stability of SBP-M13-SWNTs in blood and ascites and at different pH values was validated by measuring the fluorescence over 24 hours using a custom-built small animal NIR2 fluorescence imager. Yi H. et al., Nano Lett 2012, 12, 1176, which is incorporated by reference in its entirety. SBP-M13-SWNTs retain fluorescence at various dilutions in the blood and ascites fluid from the peritoneal cavity (FIGS. 15 and 16, respectively), and quenching of the probe was not observed. Previous reports indicate that exposed SWNTs in solution will adsorb serum proteins on their sidewall and subsequently lose fluorescence. Yi H. et al., Nano Lett 2012, 12, 1176; Cherukuri P. et al., Proc Natl Acad Sci USA 2006, 103, 18882, each of which is incorporated by reference in its entirety. Here, no loss of fluorescence intensity was observed, indicating the probes are well solubilized by M13 and highly stable for in vivo imaging applications. In addition, the probe is fluorescently stable across a broad pH range, from 4.5 to 8.5 (FIG. 17), suggesting the probes will be stable in the vascular and lymphatic systems, peritoneal cavity, and for cellular uptake. The targeted probes are well tolerated and non-cytotoxic to target OVCAR8 ovarian cell line (FIG. 18), which underscores their potential for in vivo imaging applications.

The sensitivity of the probe in terms of its capacity to target OVCAR8 ovarian cancer cells in vitro was examined. Serial ten-fold dilutions of OVCAR8 cells were incubated with SBP-M13-SWNT for 24 hours and cell lysates were collected. Measuring the fluorescence intensity of the SBP-M13-SWNT incubated cells using the custom-built imaging system, as few as approximately 10,000 cells incubated with SBP-M13-SWNT exceeded the minimum level of detection (FIG. 12c).

To test SBP-M13-SWNTs for risk of photobleaching, they were exposed to an 808 nm laser for a continuous, 30 minute period and measured fluorescence intensity in five minute intervals up to 30 minutes post-irradiation. As seen in FIG. 12d, there is no appreciable loss of fluorescence of M13-SBP-SWNTs during this period. However, the intensity of fluorescein isothiocyanate (FITC), a fluorescein derivative that has been used to molecularly image and guide intraoperative resection of ovarian tumors in humans, exponentially decreases during the same light exposure kinetics (FIG. 12d). van Dam G. M. et al., Nat Med 2011, 17, 1315, which is incorporated by reference in its entirety. The observations that SWNTs do not photobleach and also maintain their optical properties illustrate that these particles have the potential to assist surgeons to visualize tumors during resection.

Figure 19:
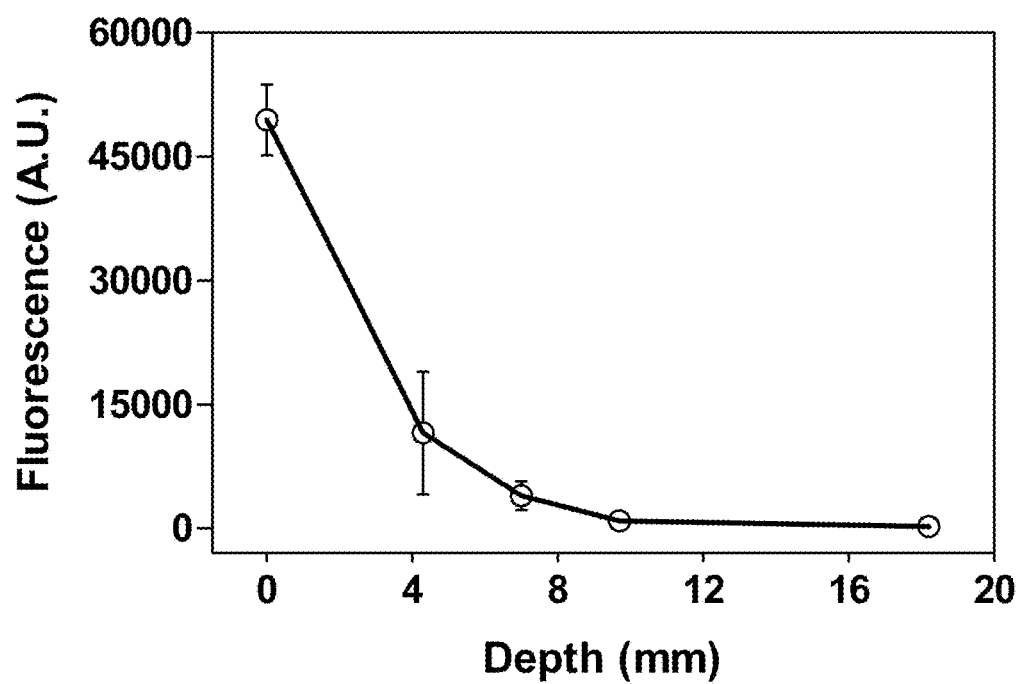
FIG. 19 illustrates depth of detection of tumors labeled with SBP-M13-SWNTs. Tumors containing SBP-M13-SWNTs were excised from mice into 1 mm diameter fragments and placed within a tissue phantom at varying known depths (0, 4.3, 7.0, 9.7, or 18.2 mm). Samples were imaged using a custom-built fluorescence imager at 0.5 s exposure. Samples were detectable to depths as great as 9.7 to 18.2 mm in the tissue phantom. Five samples were measured per condition. Error bars denote standard deviation (n=5).

Another potential advantage of SWNT-based imaging compared to FITC-based imaging is the potential to detect tumors located at greater depths in the body. To investigate the depth of detection that can be achieved with the probe, ovarian tumors that had been treated with SBP-M13-SWNTs were harvested and the small tumor fragments (~1 mm diameter) were imaged at various depths within a tissue 'phantom' construct, which mimics the optical properties of human tissue. Using the NIR2 fluorescence reflectance imaging system, SWNT-containing tumors to depths as great as 9.7 to 18.2 mm (FIG. 19) were detected. Yi H. et al., Nano Lett 2012, 12, 1176, which is incorporated by reference in its entirety. This is a better quantifiable tumor depth using reflectance imaging, relative to previously reported values. Nguyen Q. T. et al., Proc Natl Acad Sci USA 2010, 107, 4317, which is incorporated by reference in its entirety. The SBP-M13-SWNT probe, coupled with the imaging platform, allows for deeper imaging and therefore offers the potential for improved resection of tumors during surgery.

Figure 20:
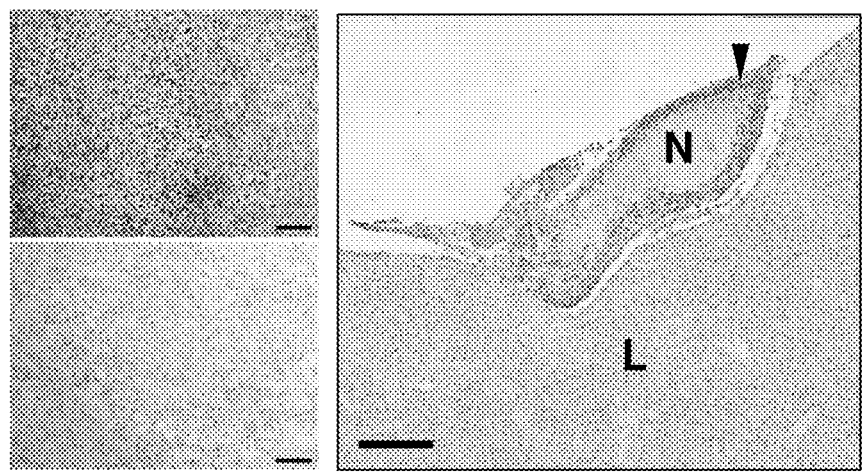
FIG. 20 illustrates SPARC Expression in OVCAR-8 Tumors. OVCAR-8 subcutaneous xenografts (left top; isotype control shown on left bottom) and orthotopic tumors (right) were processed for immunohistochemistry and examined for expression of SPARC. Both subcutaneous and orthotopic OVCAR-8 tumors express SPARC protein. Enhanced SPARC expression observed in the viable tumor rim of the orthotopic nodule (N, expression indicated by black arrow) seeded on liver (L). This is the same nodule analyzed in FIG. 13d. Scale bars: 100 µm (left top, bottom), 0.1 mm (right)

Having demonstrated the in vitro stability and fluorescence of SBP-M13-SWNTs, the in vivo properties of the probe in an orthotopic model of ovarian cancer are characterized. OVCAR8 human cell line was used to create the orthotopic model, since it overexpresses target SPARC, as confirmed by Oncomine analysis and immunohistochemistry (FIG. 20). To compare routes of administration, tumor-bearing animals were injected intraperitoneally or intravenously and the circulating probe concentration was monitored via SWNT fluorescence in the blood. Intravenously administered SBP-M13-SWNTs reached a peak concentration in the circulation approximately 10 minutes after injection, and circulating levels became negligible after 150 minutes (FIG. 12g). Notably, SBP-M13-SWNTs administered intraperitoneally led to negligible elevations in blood-borne SWNT fluorescence for at least 24 hours, suggesting that the majority of SBP-M13-SWNTs remain in the peritoneum following injection (FIG. 12g). This finding was verified by the observation that, following a transient increase in NIR2 fluorescence in the peritoneum, the overall intensity in this location stabilizes for periods up to 24 hours following injection (FIGS. 12e and 12f).

Figure 13:
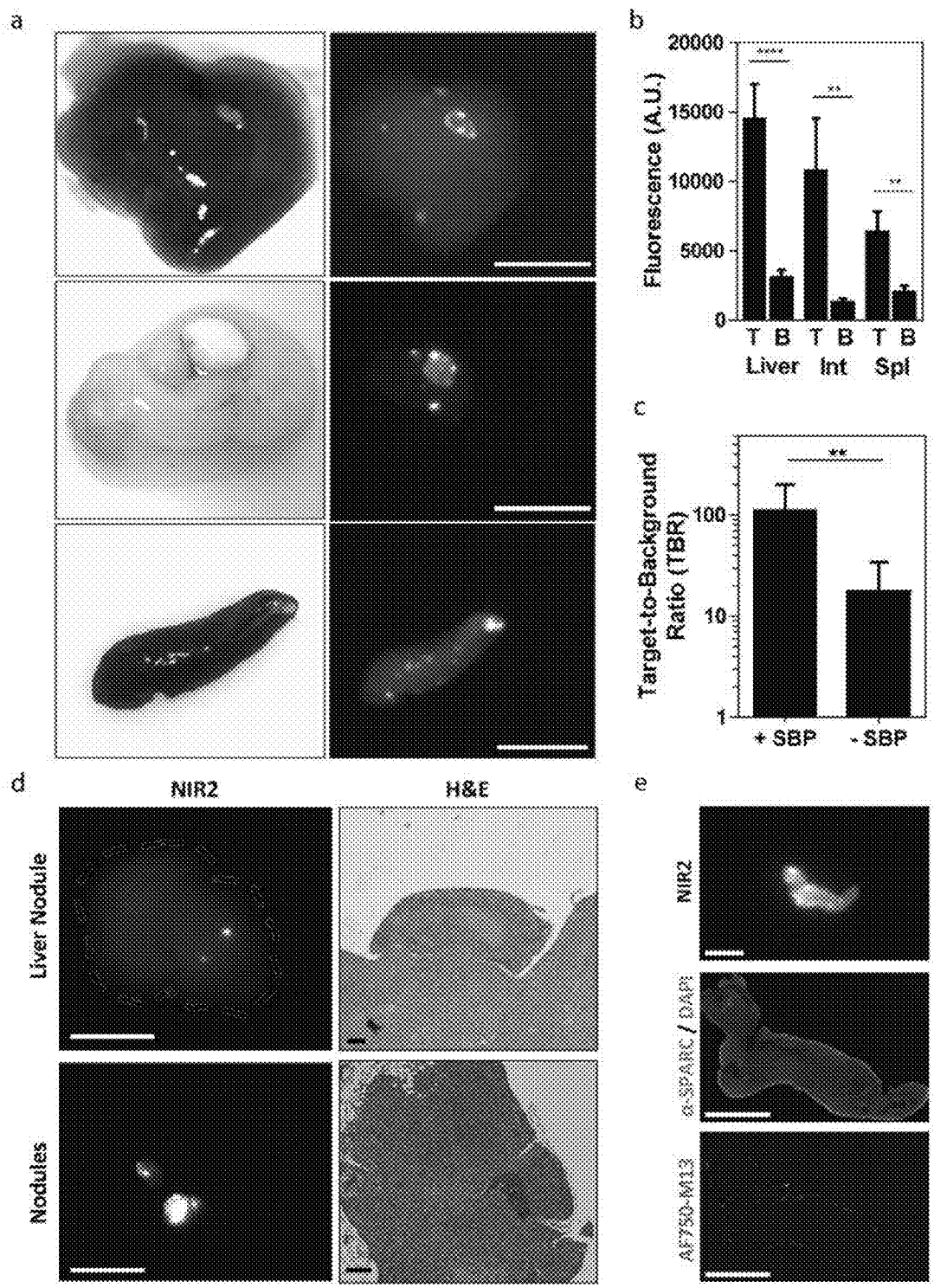
FIG. 13 illustrates specificity of M13-SBP-SWNTs for OVCAR8 Tumor Nodules in the Peritoneum. a, Photographs and NIR2 fluorescence (10-50 ms exposure) of tumor nodules implanted on several peritoneal organs. b, Quantification of nodule and organ-specific background for nodules present on the liver, intestine, and spleen. (n=8-11 nodules per organ) c, Target-to-background ratio (TBR) for targeted and untargeted probes. Intestinal tissue was used for background intensity. (+SBP, n=6; –SBP, n=13) d, Representative NIR2 fluorescence and H&E staining of a positive nodule revealing characteristic tumor histology. e, Immunofluorescence staining reveals co-localization of M13-SBP-SWNTs conjugated to AlexaFluor750 dye with SPARC expression in an NIR2-positive nodule. Scale bars: 10 mm (a), 10 mm (d, NIR2), 250 um (d, H&E Liver nodule), 125 um (d, H&E Nodules), 5 mm (e, NIR2), 2.5 mm (e, SPARC, AF750-M13)

The in vivo sensitivity of targeting conferred by the SPARC-binding peptide (SBP) was assessed by injecting tumor-bearing animals with M13-SWNTs expressing SBP or untargeted M13-SWNTs. The NIR2 intensities of excised tumor nodules and non-tumor tissues within the peritoneum of the same animal were used to compute target-to-background ratios (TBR) for the targeted and untargeted probes. SBP-M13-SWNTs showed significant, ten-fold higher TBR than untargeted M13-SWNTs, likely due to a combination of improved targeting and reduced tissue autofluorescence in the NIR2 window (FIG. 13c). Many tumor nodules are implanted on the surfaces of peritoneal organs in this model, and organ-specific TBRs for tumor nodules on the liver, intestine, and spleen were computed. Representative photographs of organs containing tumor implants on their surface with their corresponding NIR2 fluorescent images are shown in FIG. 13a. The TBRs (i.e., ratio of surface tumor nodule fluorescence relative to that observed in its underlying organ) calculated for the liver, intestine, and spleen were 4.6, 8.0, and 3.1, respectively (FIG. 13b), suggesting the specificity of the probe towards tumor nodules compared to its underlying organs.

To verify the molecular specificity of SBP-M13-SWNTs, the SWNT-positive tumor nodules was assessed by immunohistochemistry. Standard H&E staining of SWNT-positive tumor sections revealed histopathological features consistent with ovarian tumor nodules, including a high nuclear-to-cytoplasmic ratio, cellular crowding, a necrotic core, and a distinct architecture from underlying organs (FIG. 13d). Additionally, immunohistochemical staining revealed an enrichment of SPARC expression along the periphery of the SWNT-positive tumor nodules (FIG. 20). Finally, to assess whether the probe specifically co-localizes with SPARC-expressing regions of the tumor nodules, SBP-M13-SWNTs conjugated with Alexa Fluor 750 near-infrared fluorescent dye (AF750) was administered to tumor-bearing mice and the excised tumor nodules were analyzed by immunofluorescence. In multiple nodules, SPARC was widely expressed, with particularly strong expression at the tumor periphery (FIGS. 2d,e) in a pattern consistent with the immunohistochemical staining described above. The AF750-labeled SBP-M13-SWNTs were similarly enriched at the tumor periphery (FIG. 13e). These patterns are consistent with an outside-in diffusion model limited both by the hydrodynamic radius and ligand interactions of SBP-M13-SWNTs with the tumor nodule.

Figure 14:
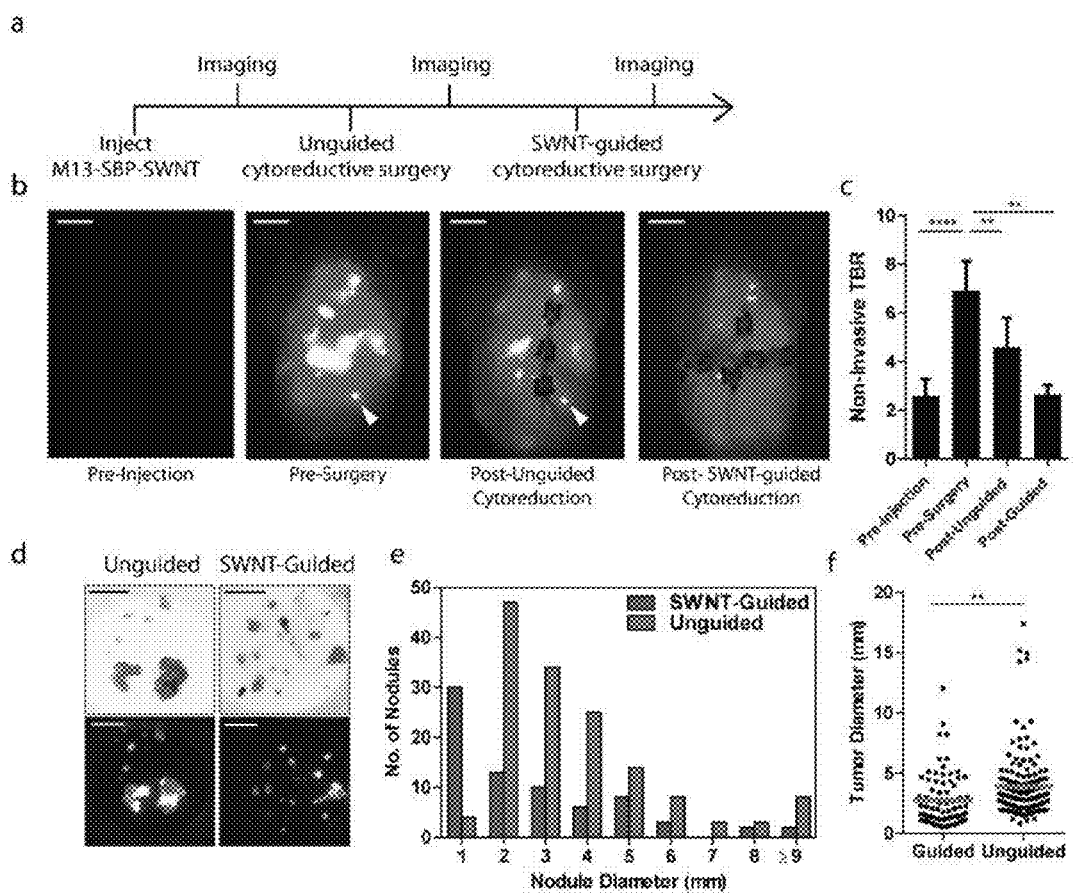
FIG. 14 illustrates cytoreductive Surgery with M13-SBP-SWNT Guidance. a, Schematic of serial surgical cytoreduction procedure. b, Representative whole-abdomen NIR2 images prior to injection of SBP-M13-SWNT, prior to surgery, after an initial, unguided cytoreduction, and after subsequent M13-SBP-SWNT-guided cytoreduction. White arrow indicates a SWNT-positive nodule detected only during image-guided cytoreduction. c, Non-invasive target-to-background ratios during cytoreduction. Muscle from hind limb used for background. d, Photographs and NIR2 images of excised tumor nodules following unguided and SWNT-guided cytoreduction. e, Histogram of tumor diameters removed with and without guidance. f, Dot plot of individual tumor nodule diameters excised with and without SWNT-guidance. Scale bars: 1 cm (b), 1 cm (c, photograph), 1 cm (c, NIR2)
Figure 21:
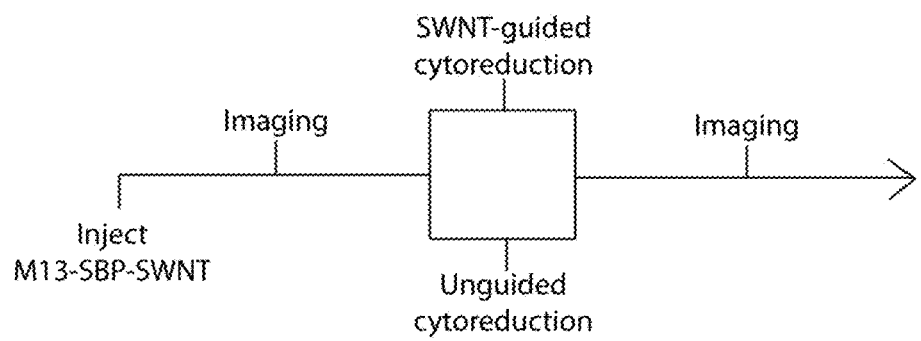
FIG. 21 illustrates comparison of SWNT-Guided and Unguided Cytoreduction. Tumor-bearing animals were randomized to receive SWNT-guided or unguided cytoreduction. Excised tumors were measured along their maximum diameters prior to tissue fixation. Tumor diameters for each treatment group are plotted as a histogram. (n=43 nodules, SWNT-guided; n=24, unguided).
Figure 21:
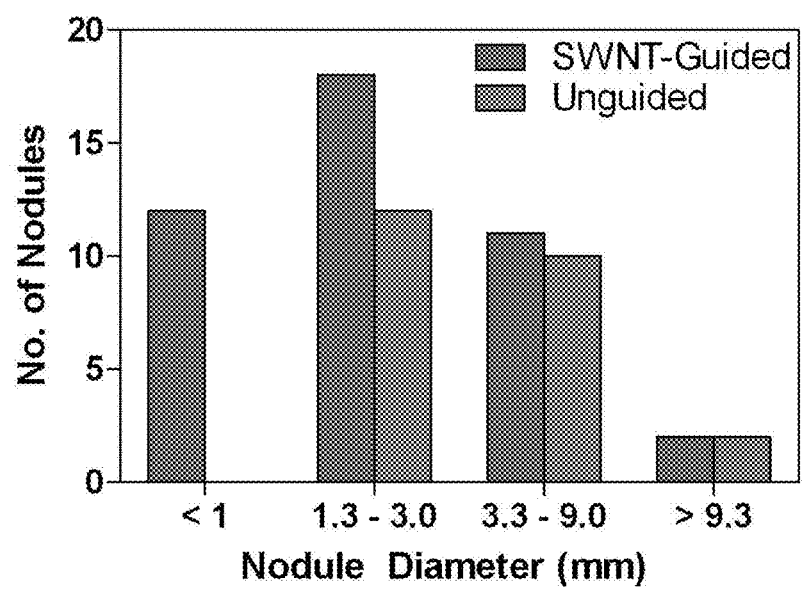

To assess the potential clinical utility of SBP-M13-SWNTs for reduction of tumor burden, a gynecologic surgeon performed cytoreductive surgeries on orthotopic models of ovarian cancer that were imaged at various points during the surgical procedures. Approximately 15-25 minutes were spent on cytoreductive procedures in each experiment, and tumor implants were predominantly distributed in the bowel mesentery, peritoneal wall, subdiaphragmatic surfaces, and surfaces of organs including the liver, spleen, pancreas, and within the pelvic cavity. H&E stained tissue sections were prepared from all excised nodules and assessed by a pathologist. With the exception of two non-tumor containing mesenteric lymph nodes, all tissues examined (n=197) were positive for ovarian tumor tissue indicating an accuracy of 98.9% of the probe for ovarian tumors. Cytoreductive surgery was first performed with pre-operative image guidance to assess whether this was beneficial to the procedure based on the distribution of excised tumor nodule sizes. A comparative analysis of excised tumors revealed that a significantly higher number of sub-millimeter tumor nodules were discovered in the image-guided cohorts versus the non-image guided cohorts (12 and 0 nodules, respectively, FIG. 21). Using image guidance, there were also greater numbers of excised tumors from 1.3 to 3 mm; however, there was no appreciable difference for larger tumors (>3 mm) between image-guided and non-guided cohorts. The impact of performing cytoreduction in a serial manner was assessed, with an initial round of non-image guided cytoreductive surgery, followed by image acquisition and a second round of image-guided cytoreductive surgery (FIG. 14a). Reduction of tumor burden from non-image guided surgery to image-guided surgery was observed (FIG. 14b). TBR of overall tumor burden to background muscle was determined by region of interest analysis and reduction of overall tumor burden due to image-guided reduction was confirmed (FIG. 14b, bar graph). Using both non-invasive SWNT imaging (FIG. 14b) and quantification of excised tumor nodule diameters, a greater number of sub-millimeter excised tumors in the groups assisted by SWNT image guidance was observed (30 versus 4 nodules, FIGS. 14c and 14d). Overall, significantly more, smaller diameter tumors were excised using SWNT-based image guidance as opposed to unguided surgeries (FIG. 14e).

What is claimed is:

1. An imaging probe, comprising:
   a photoluminescent nanostructure that emits a wavelength of light detectable through living tissue and a targeting moiety;
   wherein the photoluminescent nanostructure is complexed with the targeting moiety,
   wherein the targeting moiety comprises a first binding partner and at least one viral protein; and
   further wherein the photoluminescent nanostructure is a single walled carbon nanotube, the at least one viral protein is an M13 bacteriophage protein, and the first binding partner is selected from the group consisting of an antibody against prostate specific membrane antigen (anti-PSMA antibody), an anti-*Staphylococcus aureus* antibody, and a secreted protein acidic and rich in cysteine (SPARC)-binding peptide.

2. The imaging probe of claim 1, wherein the first binding partner binds a second binding partner, wherein the second binding partner is selected from the group consisting of a tissue-type specific molecule and a cell-type specific molecule.

3. The imaging probe of claim 2, wherein the second binding partner is a protein.

4. The imaging probe of claim 1, wherein the first binding partner is selected from the group consisting of an anti-PSMA antibody, an anti-*Staphylococcus aureus* antibody, and a fragment thereof.

5. The imaging probe of claim 1, wherein the M13 bacteriophage protein is a capsid M13 bacteriophage protein.

6. The imaging probe of claim 2, wherein the first binding partner binds the second binding partner in vivo.

7. The imaging probe of claim 2, wherein the first binding partner binds the second binding partner ex vivo.

8. The imaging probe of claim 1, wherein the imaging probe binds tumors located at various depths in the body.

9. The imaging probe of claim 1, wherein the imaging probe binds tumors located at depths of 9.7 to 18.2 millimeters below the surface of a tissue containing the tumors.

10. The imaging probe of claim 1, wherein the imaging probe differentiates between a tumor and a healthy tissue.

11. The imaging probe of claim 1, wherein the imaging probe has a fluorescence stability of at least 24 hours in vivo.

12. The imaging probe of claim 1, wherein the imaging probe fluorescence is stable at pH 4.5 to pH 8.5.

13. The imaging probe of claim 1, wherein the imaging probe is not cytotoxic to an ovarian cell line.

14. The imaging probe of claim 1, wherein the first binding partner is a SPARC-binding peptide.

15. A method comprising:
    (a) applying the imaging probe of claim 1 to a sample;
    (b) exposing at least a portion of the sample to an excitation light in order to cause an emission from the imaging probe; and
    (c) detecting the emission from the imaging probe.

16. The method of claim 15, wherein the first binding partner of the imaging probe binds a second binding partner, and wherein the second binding partner is selected from the group consisting of a tissue-type specific molecule and a cell-type specific molecule.

17. The method of claim 16, wherein the second binding partner is a protein.

18. The method of claim 15, wherein the first binding partner of the imaging probe is selected from the group consisting of an anti-PSMA antibody, an anti-*Staphylococcus aureus* antibody, and a fragment thereof.

19. The method of claim 15, wherein the M13 bacteriophage protein of the imaging probe is a capsid M13 bacteriophage protein.

20. The method of claim 15, wherein the detecting step comprises detecting the emission of the imaging probe at a wavelength between 950-1400 nm.

21. The method of claim 15, wherein the applying step comprises administering the imaging probe to a subject that is a mammal.

22. The method of claim 21, wherein the method is performed in vivo.

23. The method of claim 15, wherein the method is performed ex vivo.

24. The method of claim 15, wherein the imaging probe binds tumors located at various depths in the body.

25. The method of claim 15, wherein the imaging probe binds tumors located at depths of 9.7 to 18.2 millimeters below the surface of a tissue containing the tumors.

26. The method of claim 15, wherein the method is for image-guided surgery, and wherein detecting the emission from the imaging probe reveals tumors for surgical procedure.

27. The method of claim 26, wherein the surgical procedure is cytoreductive surgery.

28. The method of claim 26, wherein the surgical procedure is an ovarian cancer surgery.

29. The method of claim 15, wherein the imaging probe differentiates between a tumor and a healthy tissue.

30. The method of claim 15, wherein the imaging probe fluorescence is stable for at least 24 hours in vivo.

31. The method of claim 15, wherein the imaging probe fluorescence is stable at pH 4.5 to pH 8.5.

32. The method of claim 15, wherein the imaging probe is not cytotoxic to an ovarian cell line.

33. The method of claim 15, wherein the first binding partner is a SPARC-binding peptide.

* * * * *